United States Patent
Mederski et al.

(10) Patent No.: US 6,849,626 B2
(45) Date of Patent: Feb. 1, 2005

(54) AZA-AMINO ACID DERIVATIVES (FACTOR $X_A$ INHIBITORS 15)

(75) Inventors: Werner Mederski, Zwingenberg (DE); Horst Juraszyk, Seeheim-Jugenheim (DE); Dieter Dorsch, Ober-Ramstadt (DE); Christos Tsaklakidis, Weinheim (DE); Johannes Gleiltz, Darmstadt (DE); Christopher Barnes, Bad Soden (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/362,050

(22) PCT Filed: Aug. 21, 2001

(86) PCT No.: PCT/EP01/09667

§ 371 (c)(1),
(2), (4) Date: Aug. 4, 2003

(87) PCT Pub. No.: WO02/16315

PCT Pub. Date: Feb. 28, 2002

(65) Prior Publication Data

US 2004/0034072 A1 Feb. 19, 2004

(30) Foreign Application Priority Data

Aug. 21, 2000 (DE) .......................................... 100 40 783

(51) Int. Cl.$^7$ ...................... A61K 31/175; A61K 31/18; C07C 311/47; C07D 211/46; C07D 213/30

(52) U.S. Cl. .................... 514/238.5; 514/327; 514/357; 514/381; 514/467; 514/482; 514/507; 514/562; 514/590; 544/159; 546/222; 546/332; 548/253; 549/229; 560/13; 560/24; 560/29; 560/129; 560/251

(58) Field of Search .......................... 544/159; 546/222, 546/332; 548/253; 549/229; 560/13, 110, 129, 251, 24, 29; 562/439; 564/34; 514/238.5, 327, 357, 381, 467, 482, 507, 562, 590

(56) References Cited

U.S. PATENT DOCUMENTS 3,285,957 A * 11/1966 Raymond et al. ............. 564/34

FOREIGN PATENT DOCUMENTS

EP 1020434 7/2000

OTHER PUBLICATIONS

J.M. Fevig, et al, "Preparation of Meta-amidino-N,N-disubstituted Anilines as Potent Inhibitors of Coagulation Factor Xa," Bioorganic and Medical Chemistry Letters, Nov. 17, 1998, pp. 3143–3148, vol. 8, no. 22, XP004143716, ISSN: 0960–894X, table 1, Elsevier Science Publishers, Amsterdam, NL.

* cited by examiner

Primary Examiner—Fiona T. Powers
(74) Attorney, Agent, or Firm—Millen, White, Zelano & Branigan, P.C.

(57) ABSTRACT

The invention relates to semicarbazides of the general formula I

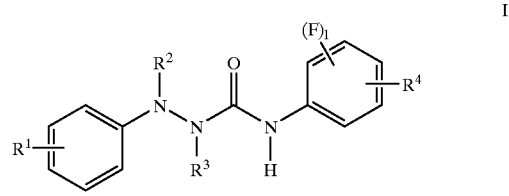

where $R^1$, $R^2$, $R^3$, $R^4$ and I have the meaning indicated in claim 1.

The compounds of the formula I can be employed as pharmaceutical active compounds in human and veterinary medicine, in particular for the control and prevention of thromboembolic disorders such as thrombosis, myocardial infarct, arteriosclerosis, inflammation, apoplexy, angina pectoris, restenosis after angioplasty and intermittent claudication.

17 Claims, No Drawings

AZA-AMINO ACID DERIVATIVES (FACTOR $X_A$ INHIBITORS 15)

The invention relates to semicarbazides of the general formula I,

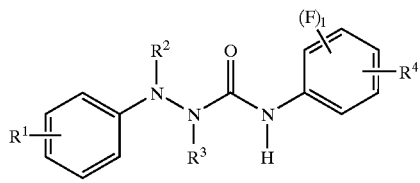

where:

$R^1$ is —$(CH_2)_n$—$NH_2$, —CON=$C(NH_2)_2$, —NHC(=NH)—$NH_2$ or —C(=NH)—$NH_2$, which can also be monosubstituted by —OH, —OCOOA, —OCOO$(CH_2)_n$N(A)$_2$, —OCOO$(CH_2)_m$—Het, —CO—$C(A)_2$—$R^5$, —COOA, —COSA, —COOAr, —COOAr'

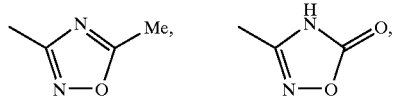

or by $R^2$ is H, COOA, $R^3$ is unbranched, branched or cyclic alkyl having 1–20 C atoms, in which one or two $CH_2$ groups can be replaced by O or S atoms, or is Ar, Ar', X or Hal, $R^4$ is phenyl monosubstituted by $S(O)_kA$, $S(O)_kNHA$, $CF_3$, COOA, $CH_2NHA$, CN or OA,

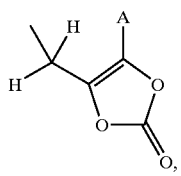

$R^5$ is —$CHal_3$, —O(C=O)A or

Ar is phenyl or naphthyl, which is unsubstituted or mono-, di- or trisubstituted by A, OH, OA, $NH_2$, NHA, $NA_2$, $NO_2$, $CF_3$, CN, Hal, NHCOA, COOA, $CONH_2$, CONHA, $CONA_2$, $S(O)_nA$, $S(O)_nNH_2$, $S(O)_nNHA$, $S(O)_nNA_2$, Ar' is —$(CH_2)_n$—Ar, Het is a mono- or binuclear, saturated, unsaturated or aromatic heterocycle having 1 to 4 N, O and/or S atoms, bonded via N or C, which can be unsubstituted or substituted by A, A is H, unbranched, branched or cyclic alkyl having 1–20 C atoms, X is —$(CH_2)_n$—Y,

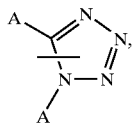

Y is COOA,

Hal is F, Cl, Br or I, n is 1, 2, 3, 4, 5 or 6, m is 0 or 1, k is 0, 1 or 2, l is 0, 1, 2, 3 or 4, and their pharmaceutically tolerable salts and solvates.

The invention also relates to the optically active forms, the racemates, the diastereomers and also the hydrates and solvates, e.g. alcoholates, of these compounds.

For the control of hemorrhages caused by injuries, the human body has a mechanism by means of which, with the aid of blood clots, a rapid wound closure is achieved. Blood clots are formed by a series of zymogen activations. In the course of this enzymatic cascade, the activated form of a factor in each case catalyzes the activation of the next. Since this process is of catalytic nature, very small amounts of the triggering factor suffice to set the cascade in motion. As a result of the large number of steps, a large amplification is achieved, which guarantees a rapid response to the injury. The plasmatic clotting after a tissue lesion can take place exogenously due to the release of tissue thrombokinase. The corresponding reaction sequence is designated as an extravascular system (extrinsic system) and proceeds within seconds. The clotting can also be triggered endogenously by thrombocytolysis. This reaction sequence, which is designated as an intravascular system, proceeds within minutes. Both systems result in a final common sequence of steps which lead to the formation of a blood clot. The intravascular and the extravascular system have a mutual influence in vivo. Both are necessary for the complete course of blood clotting.

Rapid blood clotting is so important for the closure of injuries, in certain disorders it is actually necessary to inhibit blood clotting in order, for example, to avoid the formation of thrombi in vessels. In this case, an intervention should be made as specifically and selectively as possible into the blood clotting cascade in order to be able to control the inhibition as precisely as possible and to be able to avoid undesired side effects.

Factor $X_a$ is a serine protease of the blood clotting cascade, which is formed by activation of factor X. In the intravascular pathway, this activation is carried out by factor $IX_a$, this reaction being stimulated by the antihemophilic factor ($VIII_a$). By means of factor $X_a$, prothrombin is then converted into thrombin. The proteolytic enzyme thrombin cleaves fibrinogen into fibrin monomers, which arrange spontaneously to give ordered fibrous structures, which are designated as fibrin. The clot that results due to the spontaneous aggregation of fibrin monomers is stabilized by covalent crosslinkages between the side chains of various molecules in the fibrin fibers. To this end, peptide bonds are formed between specific glutamine and lysine side chains in a transamidation reaction. This crosslinkage is catalyzed by an enzyme which is designated as factor $XIII_a$.

In the extravascular system, the activation of factor X is carried out by the tissue factor and factor VII.

Inhibition of factor $X_a$ allows specific intervention into blood clotting, since no other processes are influenced here. It is more advantageous than, for example, inhibition of thrombin, since thrombin on the one hand catalyzes the conversion of fibrinogen to fibrin, and also the conversions of factor VIII into factor $VIII_a$, factor V into $V_a$ and factor XI into $XI_a$, and on the other hand, for example, also activates platelets. A variety of research activities have therefore been undertaken to develop inhibitors of factor $X_a$, which have led to the development of various classes of substance.

WO 99/11657 describes 1-amino-7-isoquinoline derivatives which act as inhibitors of serine proteases. WO 99/11658 describe m-benzamidine derivatives which act as serine protease inhibitors. Furthermore, WO 99/10316 describes 3-amidinoaniline derivatives which act as inhibitors of activated blood clotting factor $X_a$.

It is an object of the invention to discover novel compounds having valuable properties, in particular those which can be used for the production of medicaments.

It has been found that the compounds of the formula I and their salts have very valuable pharmacological properties, together with good tolerability. In particular, they exhibit factor $X_a$-inhibiting properties and can therefore be employed for the control and prevention of thromboembolic disorders, such as thrombosis, myocardial infarct, arteriosclerosis, inflammation, apoplexy, angina pectoris, restenosis after angioplasty and intermittent claudication.

The compounds of the formula I according to the invention can furthermore be inhibitors of the blood clotting factors $VII_a$, $IX_a$ and thrombin of the blood clotting cascade.

The inhibition of thrombin can be measured, for example, by the method of G. F. Cousins et al. in *Circulation* 1996, 94, 1705–1712.

The inhibition of factor $X_a$ by the compounds according to the invention and the measurement of the anticoagulant and antithrombotic activity can be determined according to customary in vitro or in vivo methods. A suitable procedure is described, for example, by J. Hauptmann et al. in *Thrombosis and Haemostasis*, 1990, 63, 220–223.

The measurement of the inhibition of factor $X_a$ can be carried out, for example, according to the method of T. Hara et al. in *Thromb. Haemostas.*, 1994, 71, 314–319.

The inhibition of factor $VII_a$ by the compounds according to the invention and the measurement of the anticoagulant and antithrombotic activity can be determined according to customary in vitro or in vivo methods. A customary procedure for the measurement of the inhibition of factor $VII_a$ is described, for example, by H. F. Ronning et al. in *Thrombosis Research* 1996, 84, 73–81.

The inhibition of factor $IX_a$ by the compounds according to the invention and the measurement of the anticoagulant and antithrombotic activity can be determined according to customary in vitro or in vivo methods. A suitable procedure is described, for example, by J. Chang et al. in *Journal of Biological Chemistry* 1998, 273, 12089–12094.

The compounds of the formula I can be employed as pharmaceutical active compounds in human and veterinary medicine, in particular for the control and prevention of thromboembolic disorders such as thrombosis, myocardial infarct, arteriosclerosis, inflammation, apoplexy, angina pectoris, restenosis after angioplasty and/or intermittent claudication. Furthermore, they are applicable for the treatment of tumors, tumor diseases and/or tumor metastases. A relation between the tissue factor TK/factor VIIa and the development of various types of cancer has been shown by T. Taniguchi et al. in Biomed. Health Res. (2000), 41 ("Molecular Pathogenesis of Pancreatic Cancer"), 57–59.

The semicarbazides according to the invention particularly preferably have a structure of the formula II

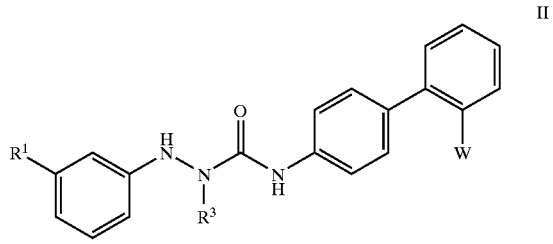

where $R^1$, $R^3$, A and k have the meaning indicated in claim 1 and W is $S(O)_kA$, $S(O)_kNHA$, $CF_3$, COOA, $CH_2NHA$, CN or OA.

Compounds which are particularly to be emphasized are mentioned below:

4'-[3-(3-amidinophenyl)-2-propylcarbazoylamino] biphenyl-2-sulfonamide (1),

4'-[3-(3-($N^2$-hydroxyamidino)phenyl)-2-propylcarbazoylamino]biphenyl-2-sulfonamide (2), 4'-[3-(3-amidinophenyl)-2-methylcarbazoylamino] biphenyl-2-sulfonamide (3), 1-(3-amidinophenyl)-2-methyl-4-(2'-methylsulfonylbiphenyl-4-yl)semicarbazide (4), 4'-[3-(3-amidinophenyl)-2-ethylcarbazoylamino] biphenyl-2-sulfonamide (5), 1-(3-amidinophenyl)-2-ethyl4-(2'-methylsulfonylbiphenyl4-yl)semicarbazide (6), 4'-[3-(3-amidinophenyl)-2-isopropylcarbazoylamino] biphenyl-2-sulfonamide (7), 1-(3-amidinophenyl)-2-isopropyl-4-(2'-methylsulfonylbiphenyl-4-yl)semicarbazide (8), 4'-[3-(3-amidinophenyl)-2-butylcarbazoylamino] biphenyl-2-sulfonamide (9), 1-(3-amidinophenyl)-2-butyl-4-(2'-methylsulfonylbiphenyl-4-yl)semicarbazide (10), 4'-[3-(3-amidinophenyl)-2-isobutylcarbazoylamino] biphenyl-2-sulfonamide (11), 1-(3-amidinophenyl)-2-isobutyl4-(2'-methylsulfonylbiphenyl-4-yl)semicarbazide (12), 4'-[3-(3-amidinophenyl)-2-pentylcarbazoylamino] biphenyl-2-sulfonamide (13), 1-(3-amidinophenyl)-4-(2'-methylsulfonylbiphenyl-4-ylamino)-2-pentylsemicarbazide (14), 1-(3-amidinophenyl)-4-(2'-methylsulfonylbiphenyl-4-ylamino)-2-propylsemicarbazide (15), 4'-[3-(3-amidinophenyl)-2-(2-butyl)carbazoylamino] biphenyl-2-sulfonamide (16), 1-3-amidinophenyl)-2-(2-butyl)-4-(2'-methylsulfonylbiphenyl-4-yl)semicarbazide (17), 4'-[3-(3-amidinophenyl)-2-(cyclohexylmethyl) carbazoylamino]biphenyl-2-sulfonamide (18), 1-(3-amidinophenyl)-2-(cyclohexylmethyl)-4-(2'-methylsulfonylbiphenyl-4-yl)semicarbazide (19), 4'-[3-(3-amidinophenyl)-2-benzylcarbazoylamino] biphenyl-2-sulfonamide (20), 1-(3-amidinophenyl)-2-benzyl-4-(2'-methylsulfonylbiphenyl-4-yl)semicarbazide (21), 1-(3-N-2-hydroxyamidinophenyl)-2-benzyl-4-(2'-methylsulfonylbiphenyl-4-yl)semicarbazide (22), 4'-[3-(3-amidinophenyl)-2-phenylcarbazoylamino] biphenyl-2-sulfonamide (23), 1-(3-amidinophenyl)-4-(2'-methylsulfonylbiphenyl-4-yl)-2-phenylsemicarbazide (24), methyl N-[3-[2-benzyl-4-(2'-methylsulfonylbiphenyl-4-yl)semicarbazido]-phenyl(iminomethyl)]carbamate (25), 2,2,2-trichloroethyl N-[3-[2-benzyl-4-(2'-methylsulfonylbiphenyl-4-yl)semicarbazido]phenyl(iminomethyl)]carbamate (26), S-ethyl N-[3-[2-benzyl-4-(2'-methylsulfonylbiphenyl-4-yl)semicarbazido]-phenyl(iminomethyl)] thiocarbamate (27), 4-methoxybenzyl N-[3-[2-benzyl-4-(2'-methylsulfonylbiphenyl-4-yl)semicarbazido]phenyl(iminomethyl)]carbamate (28), ethyl N-[3-[2-benzyl-4-(2'-methylsulfonylbiphenyl-4-yl)semicarbazido]-phenyl(iminomethyl)]carbamate (29), propyl N-[3-[2-benzyl-4-(2'-methylsulfonylbiphenyl-4-yl)semicarbazido]-phenyl(iminomethyl)]carbamate (30), butyl N-[3-[2-benzyl-4-(2'-methylsulfonylbiphenyl-4-yl)semicarbazido]-phenyl(iminomethyl)]carbamate (31), isopropyl N-[3-[2-benzyl-4-(2'-methylsulfonylbiphenyl-4-yl)semicarbazido]phenyl(iminomethyl))carbamate (32), isobutyl N-[3-[2-benzyl-4-(2'-methylsulfonylbiphenyl-4-yl)semicarbazido]-phenyl(iminomethyl)]carbamate (33), allyl N-[3-[2-benzyl-4-(2'-methylsulfonylbiphenyl-4-yl) semicarbazido]-phenyl(iminomethyl)]carbamate (34), phenyl N-[3-[2-benzyl-4-(2'-methylsulfonylbiphenyl-4-yl)semicarbazido]-phenyl(iminomethyl)]carbamate (35), 2-fluorophenyl N-[3-[2-benzyl4-(2'-methylsulfonylbiphenyl4-yl)semicarbazido]phenyl(iminomethyl)]carbamate (36), 2-benzyl-1-[3-(N$^1$-(methylcarboxy)amidino)phenyl]4-(2'-methylsulfonylbiphenyl-4-yl)semicarbazide (37), 2-benzyl-4-(2'-methylsulfonylbiphenyl-4-yl)-1-[3-(N$^1$-(phenylcarboxy)amidino)phenyl]semicarbazide (38), 2-benzyl-1-[3-(N$^1$-(isobutylcarboxy)amidino)phenyl]-4-(2'-methylsulfonylbiphenyl-4-yl)semicarbazide (39), 2-benzyl-1-[3-[N$^1$-(2-methylcarboxy-2-propoxycarbonyl)amidino]phenyl]-4-(2'-methylsulfonylbiphenyl-4-yl)semicarbazide (40), 2-benzyl-1-[3-[N$^1$-(1-(methylcarboxy)ethoxycarbonyl) amidino]phenyl]-4-(2'-methylsulfonylbiphenyl-4-yl) semicarbazide (41), 1-methyl-4-piperidinyl N-[3-[2-benzyl-4-(2'-methylsulfonylbiphenyl-4-yl)semicarbazido]phenyl(iminomethyl)]carbamate (42), 2-(4-pyridyl)ethyl N-[3-[2-benzyl-4-(2'-methylsulfonylbiphenyl-4-yl)semicarbazido]phenyl(iminomethyl)]carbamate (43), 5-methyl-2-oxo-1,3-dioxol-4-ylmethyl N-[3-[2-benzyl-4-(2'-methylsulfonylbiphenyl-4-yl)semicarbazido] phenyl(iminomethyl)]carbamate (44), 2-(3-pyridyl)ethyl N-[3-[2-benzyl-4-(2'-methylsulfonylbiphenyl-4-yl)semicarbazido]phenyl(iminomethyl)]carbamate (45), 2-(N,N-diethylamino)ethyl N-[3-[2-benzyl-4-(2'-methylsulfonylbiphenyl-4-yl)semicarbazido]phenyl(iminomethyl)]carbamate (46), 2-(N-morpholinyl)ethyl N-[3-[2-benzyl-4-(2'-methylsulfonylbiphenyl-4-yl)semicarbazido]phenyl (iminomethyl)]carbamate (47), 1-(3-amidinophenyl)-2-(2-fluorobenzyl)-4-(2'-methylsulfonylbiphenyl-4-yl)semicarbazide (48), 1-(3-amidinophenyl)-2-(2-methylbenzyl)-4-(2'-methylsulfonylbiphenyl4-yl)semicarbazide (49), 1-(3-amidinophenyl)-2-(2-chlorobenzyl)-4-(2'-methylsulfonylbiphenyl4-yl)semicarbazide (50), 1-(3-amidinophenyl)-2-(3-chlorobenzyl)-4-(2'-methylsulfonylbiphenyl-4-yl)semicarbazide (51), 4-[1-(3-amidinophenylamino)-3-(2'-methylsulfonylbiphenyl-4-yl)ureidomethyl]-benzoic acid (52), 1-(3-amidinophenyl)-2-(3-methylbenzyl)-4-(2'-methylsulfonylbiphenyl-4-yl)semicarbazide (53), 1-(3-amidinophenyl)-4-(2'-methylsulfonylbiphenyl-4-yl)-2-(3-trifluoromethyl -benzyl)semicarbazide (54), 1-(3-amidinophenyl)-4-(2'-methylsulfonylbiphenyl-4-yl)-2-(4-trifluoromethyl -benzyl)semicarbazide (55), 1-(3-amidinophenyl)-4-(2'-methylsulfonylbiphenyl-4-yl)-2-(3-trifluoromethoxy -benzyl)semicarbazide (56), 1-(3-amidinophenyl)-2-benzyl-4-(2'-methylsulfonyl-3-fluor-biphenyl-4-yl)-semicarbazide (57), 1-(3-amidinophenyl)-2-(3-trifluormethylbenzyl)-4-(2'-methylsulfonyl-3-fluor-biphenyl-4-yl)-semicarbazide (58), 1-(3-amidinophenyl)-2-(4-trifluormethylbenzyl)-4-(2'-methylsulfonyl-3-fluor-biphenyl-4-yl)-semicarbazide (59), 1-(3-amidinophenyl)-2-(2-trifluormethylbenzyl)-4-(2'-methylsulfonylbiphenyl-4-yl)-semicarbazide (60), 1-(3-amidinophenyl)-2-(2-trifluormethylbenzyl)-4-(2'-methylsulfonyl-3-fluor-biphenyl-4-yl)-semicarbazide (61), 1-(3-amidinophenyl)-2-benzyl-4-(2'-methylsulfonyl-3,5-difluor-biphenyl-4-yl)-semicarbazide (62), 1-(3-amidinophenyl)-2-(2-trifluormethylbenzyl)-4-(2'-methylsulfonyl-3,5-difluor-biphenyl-4-yl)-semicarbazide (63), 1-(3-amidinophenyl)-2-(3-trifluormethylbenzyl)-4-(2'-methylsulfonyl-3,5-difluor-biphenyl-4-yl)-semicarbazide (64), 1-(3-amidinophenyl)-2-(4-trifluormethylbenzyl)-4-(2'-methylsulfonyl-3,5-difluor-biphenyl-4-yl)-semicarbazide (65), ethyl 2-[1-(3-amidinophenylamino)-3-(2'-sulfamoylbiphenyl-4-yl)ureido]-acetate (66), ethyl 3-[1-(3-amidinophenylamino)-3-(2'-sulfamoylbiphenyl-4-yl)ureido]-propionate (67), 4'-[3-(3-amidinophenyl)-2-[2-(1-methyltetrazol-5-yl) ethyl]carbazoylamino]-biphenyl-2-sulfonamide (68), 4'-[3-(3-amidinophenyl)-2-(2-methoxyethyl) carbazoylamino]biphenyl-2-sulfonamide (69), 4'-[3-(3-amidinophenyl)-2-(methoxymethyl) carbazoylamino]biphenyl-2-sulfonamide (70), 4'-[3-(3-amidinophenyl)-2-(4-methoxybutyl) carbazoylamino]biphenyl-2-sulfonamide (71), 1-(3-aminomethylphenyl)-2-benzyl-4-(2'-methylsulfonylbiphenyl-4-yl)semicarbazide (72), 1-(3-aminomethylphenyl)-4-(2'-methylsulfonylbiphenyl-4-yl)-2-(2-trifluoro -methylbenzyl)semicarbazie (73), 1-(3-aminomethylphenyl)-4-(2'-methylsulfonylbiphenyl-4-yl)-2-(3-trifluoro-methylbenzyl)semicarbazie (74),
1-(3-aminomethylphenyl)-4-(2'-methylsulfonylbiphenyl-4-yl)-2-(4-trifluoro-methylbenzyl)semicarbazie (75),
1-(3-aminomethylphenyl)-2-benzyl-4-(3-fluoro-2'-methylsulfonylbiphenyl-4-yl)semicarbazide (76),
1-(3-aminomethylphenyl)-4-(3-fluoro-2'-methylsulfonylbiphenyl-4-yl)-2-(2-trifluoromethylbenzyl)semicarbazide (77),
1-(3-aminomethylphenyl)-4-(3-fluoro-2'-methylsulfonylbiphenyl-4-yl)-2-(3-trifluoromethylbenzyl)semicarbazide (78),
1-(3-aminomethylphenyl)-4-(3-fluoro-2'-methylsulfonylbiphenyl-4-yl)-2-(4-trifluoromethylbenzyl)semicarbazide (79).
1-(3-aminomethylphenyl)-2-(3-trifluoromethylbenzyl)-4-(2'-methylsulfonylbiphenyl-4-yl)-semicarbazide (80),
1-(3-aminomethylphenyl)-2-(4-trifluoromethylbenzyl)-4-(2'-methylsulfonylbiphenyl-4-yl)-semicarbazide (81),
1-(3-aminomethylphenyl)-2-benzyl-4-(2'-methylsulfonyl-3-fluoro-biphenyl-4-yl)-semicarbazide (82),
1-(3-aminomethylphenyl)-2-(3-trifluoromethylbenzyl)-4-(2'-methylsulfonyl-3-fluoro-biphenyl-4-yl)-semicarbazide (83),
1-(3-aminomethylphenyl)-2-benzyl-4-(2'-methylsulfonylbiphenyl-4-yl)-semicarbazide (84),
1-(3-aminomethylphenyl)-2-(2-trifluoromethylbenzyl)-4-(2'-methylsulfonyl-3-fluoro-biphenyl-4-yl)-semicarbazide (85),
1-(3-aminomethylphenyl)-2-benzyl-4-(2'-methylsulfonyl-3,5-difluoro-biphenyl-4-yl)-semicarbazide (86),
1-(3-aminomethylphenyl)-2-(2-trifluoromethylbenzyl)-4-(2'-methylsulfonyl-3,5-difluoro-biphenyl-4-yl)-semicarbazide (87),
1-(3-aminomethylphenyl)-2-(4-trifluoromethylbenzyl)-4-(2'-methylsulfonyl-3,5-difluoro-biphenyl-4-yl)-semicarbazide (88),
2-Benzyl-1-[3-($N^1$-methoxy)-amidino)-phenyl]-4-(2'-methylsulfonylbiphenyl-4-yl)-semicarbazide (89),
2-Benzyl-1-[3-(N1-ethoxy)-amidino)-phenyl]-4-(2'-methylsulfonylbiphenyl-4-yl)-semicarbazide (90),
2-Benzyl-1-[3-(N1-vinyloxy)-amidino)-phenyl]-4-(2'-methylsulfonylbiphenyl-4-yl)-semicarbazide (91),
2-Benzyl-1-[3-(N1-benzyloxy)-amidino)-phenyl]-4-(2'-methylsulfonylbiphenyl-4-yl)-semicarbazide (92),
2-Benzyl-1-[3-(N1-isopropoxy)-amidino)-phenyl]-4-(2'-methylsulfonylbiphenyl-4-yl)-semicarbazide (93),
1-[3-(N-Hydroxyamidino)-phenyl]-2-(3-trifluoromethylbenzyl)-4-(2'-methylsulfonylbiphenyl-4-yl)-semicarbazide (94),
1-[3-(N-Hydroxyamidino)-phenyl]-2-(4-trifluoromethylbenzyl)-4-(2'-methylsulfonylbiphenyl-4-yl)-semicarbazide (95),
1-[3-(N-Hydroxyamidino)-phenyl]-2-benzyl-4-(2'-methylsulfonyl-3-fluorobiphenyl-4-yl)-semicarbazide (96),
1-[3-(N-Hydroxyamidino)-phenyl]-2-(3-trifluoromethylbenzyl)-4-(2'-methylsulfonyl-3-fluorobiphenyl-4-yl)-semicarbazide (97),
1-[3-(N-Hydroxyamidino)-phenyl]-2-(4-trifluoromethylbenzyl)-4-(2'-methylsulfonyl-3-fluorobiphenyl-4-yl)-semicarbazide (98),
1-[3-(N-Hydroxyamidino)-phenyl]-2-(2-trifluoromethylbenzyl)-4-(2'-methylsulfonylbiphenyl-4-yl)-semicarbazide (99),
1-[3-(N-Hydroxyamidino)-phenyl]-2-(2-trifluoromethylbenzyl)-4-(2'-methylsulfonyl-3-fluorobiphenyl-4-yl)-semicarbazide (100),
1-[3-(N-Hydroxyamidino)-phenyl]-2-benzyl-4-(2'-methylsulfonyl-3,5-difluorobiphenyl-4-yl)-semicarbazide (101),
1-[3-(N-Hydroxyamidino)-phenyl]-2-(2-trifluoromethylbenzyl)-4-(2'-methylsulfonyl-3,5-difluoro-biphenyl-4-yl)-semicarbazide (102),
1-[3-(N-Hydroxyamidino)-phenyl]-2-(3-trifluoromethylbenzyl)-4-(2-methylsulfonyl-3,5-difluoro-biphenyl-4-yl)-semicarbazide (103),
1-[3-(N-Hydroxyamidino)-phenyl]-2-(4-trifluoromethylbenzyl)-4-(2-methylsulfonyl-3,5-difluoro-biphenyl-4-yl)-semicarbazide (104).

Particular embodiments of the compounds of the formula I are mentioned below, a generalized form of the group of compounds being indicated in the tables.

The coefficients indicated in the formulae correspond to the meanings indicated above. In the case of the examples synthesized for the individual groups of compounds, the FAB values measured are indicated in each case if available.

In table 1, examples are mentioned for compounds in which the various alkyl radicals $R^3$ are introduced into the molecular structure. In the diphenyl moiety, the sulfonamide derivatives and the methylsulfonyl derivatives were prepared by variation of the group Y, which is an amino or a methyl group.

TABLE 1

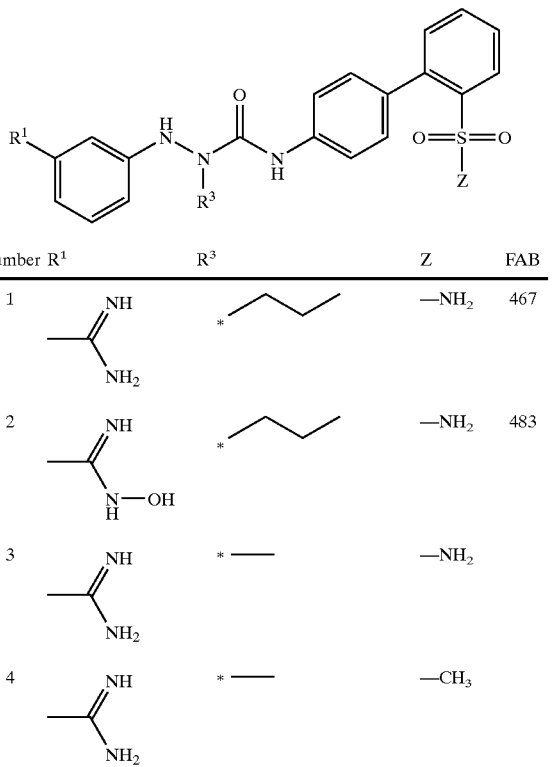

| Number | $R^1$ | $R^3$ | Z | FAB |
|---|---|---|---|---|
| 1 | —C(=NH)NH₂ | propyl | —NH₂ | 467 |
| 2 | —C(=NH)NH—OH | propyl | —NH₂ | 483 |
| 3 | —C(=NH)NH₂ | * — | —NH₂ | |
| 4 | —C(=NH)NH₂ | * — | —CH₃ | |

TABLE 1-continued

[Structure: R¹-NH-N(R³)-C(=O)-NH-C₆H₄-C₆H₄-SO₂-Z]

| Number | R¹ | R³ | Z | FAB |
|---|---|---|---|---|
| 5 | C(=NH)NH₂ | ethyl (propyl) | —NH₂ | |
| 6 | C(=NH)NH₂ | propyl | —CH₃ | |
| 7 | C(=NH)NH₂ | isopropyl | —NH₂ | |
| 8 | C(=NH)NH₂ | isopropyl | —CH₃ | |
| 9 | C(=NH)NH₂ | butyl | —NH₂ | |
| 10 | C(=NH)NH₂ | butyl | —CH₃ | |
| 11 | C(=NH)NH₂ | isobutyl | —NH₂ | |
| 12 | C(=NH)NH₂ | isobutyl | —CH₃ | |
| 13 | C(=NH)NH₂ | —(CH₂)₄NH₂ | —NH₂ | |
| 14 | C(=NH)NH₂ | hexyl | —CH₃ | |
| 15 | C(=NH)NH₂ | butyl | —CH₃ | 446 |

Examples in which the radical R³ is constructed as a cycloalkyl radical or as an aromatic radical are shown in table 2. Here too, sulfonamide derivatives and methylsulfonyl derivatives were prepared by variation of the group Z.

TABLE 2

[Structure: R¹-NH-N(R³)-C(=O)-NH-C₆H₄-C₆H₄-SO₂-Z]

| Number | R¹ | R³ | Z | FAB |
|---|---|---|---|---|
| 16 | C(=NH)NH₂ | sec-butyl | —NH₂ | |
| 17 | C(=NH)NH₂ | sec-butyl | —NH₂ | |
| 18 | C(=NH)NH₂ | CH₂-cyclohexyl | —NH₂ | |
| 19 | C(=NH)NH₂ | CH₂-cyclohexyl | —CH₃ | |
| 20 | C(=NH)NH₂ | CH₂-phenyl | —NH₂ | 515 |
| 21 | C(=NH)NH₂ | CH₂-phenyl | —CH₃ | 514 |
| 22 | C(=NH)N(H)OH | CH₂-phenyl | —CH₃ | 530 |
| 23 | C(=NH)NH₂ | phenyl | —NH₂ | |
| 24 | C(=NH)NH₂ | phenyl | —CH₃ | |

The compounds of the formula I can also be constructed as prodrugs. After absorption into the blood circulation, the compounds are cleaved enzymatically and the active compound is released. In table 3, various possibilities for prodrugs are presented with the aid of an active compound.

The absorption rate and the rate of release of the active compound, for example, can be influenced by the variation of the radical R¹. The examples of the group R¹ indicated in table 3 can be transferred without problems to other active compounds of the formula I, such as, for example, are shown in tables 1 and 2.

TABLE 3

[Structure: R¹—NH—N(CH₂Ph)—C(=O)—NH—C₆H₄—C₆H₄—SO₂CH₃]

| Number | R¹ | FAB |
|---|---|---|
| 25 | *—C(=NH)—NH—C(=O)—O—CH₃ | 572 |
| 26 | *—C(=NH)—NH—C(=O)—O—CH₂CCl₃ | 690 |
| 27 | *—C(=NH)—NH—C(=O)—S—ethyl | — |
| 28 | *—C(=NH)—NH—C(=O)—O—CH₂—C₆H₄—OCH₃ | 678 |
| 29 | *—C(=NH)—NH—C(=O)—O—ethyl | 586 |
| 30 | *—C(=NH)—NH—C(=O)—O—propyl | — |
| 31 | *—C(=NH)—NH—C(=O)—O—butyl | 614 |
| 32 | *—C(=NH)—NH—C(=O)—O—isopropyl | 600 |
| 33 | *—C(=NH)—NH—C(=O)—O—isobutyl | 614 |

TABLE 3-continued

[Structure: R¹—NH—N(CH₂Ph)—C(=O)—NH—C₆H₄—C₆H₄—SO₂CH₃]

| Number | R¹ | FAB |
|---|---|---|
| 34 | *—C(=NH)—NH—C(=O)—O—allyl | 598 |
| 35 | *—C(=NH)—NH—C(=O)—O—phenyl | 634 |
| 36 | *—C(=NH)—NH—C(=O)—O—(4-F-C₆H₄) | 652 |

Further examples of variation of the radical R¹ for preparation of prodrugs are indicated in table 4. The preparation of the prodrugs shown in tables 3 and 4 is carried out analogously to the procedures which are described in S. N. Rahamthullah et al J. Med. Chem. 1999, 42, 3994–4000.

TABLE 4

[Structure: R¹—NH—N(CH₂Ph)—C(=O)—NH—C₆H₄—C₆H₄—SO₂CH₃]

| Number | R¹ | FAB |
|---|---|---|
| 37 | *—C(=NH)—NH—O—C(=O)—CH₃ | 572 |
| 38 | *—C(=NH)—NH—O—C(=O)—C₆H₅ | 634 |

TABLE 4-continued

[Structure shown with R¹ group, hydrazide linker, benzyl, urea, and biphenyl methylsulfonyl moiety]

| Number | R¹ | FAB |
|--------|----|----|
| 39 | *-C(=NH)-NH-O-CH₂-C(=O)-O-CH₂-CH(CH₃)₂ | 614 |
| 40 | *-C(=NH)-NH-C(=O)-O-C(CH₃)₂-O-C(=O)-CH₃ | 672 |
| 41 | *-C(=NH)-NH-C(=O)-O-CH(CH₃)-O-C(=O)-CH₃ | |
| 42 | *-C(=NH)-NH-C(=O)-O-(N-methylpiperidin-4-yl) | 692 |
| 43 | *-C(=NH)-NH-C(=O)-O-CH₂CH₂-(pyridin-4-yl) | |
| 44 | *-C(=NH)-NH-C(=O)-O-CH₂-(4-methyl-5-oxo-1,3-dioxol-4-en-yl) | |
| 45 | *-C(=NH)-NH-C(=O)-O-CH₂CH₂-(pyridin-3-yl) | |
| 46 | *-C(=NH)-NH-C(=O)-O-CH₂CH₂-N(CH₂CH₃)₂ | |

TABLE 4-continued

[Same parent structure]

| Number | R¹ | FAB |
|--------|----|----|
| 47 | *-C(=NH)-NH-C(=O)-O-CH₂CH₂-(morpholin-4-yl) | |
| 89 | *-C(=NH)-NH-O-CH₃ | |
| 90 | *-C(=NH)-NH-O-CH₂CH₃ | |
| 91 | *-C(=NH)-NH-O-CH=CH₂ | |
| 92 | *-C(=NH)-NH-O-CH₂-C₆H₅ | |
| 99 | *-C(=NH)-NH-O-CH₂-CH(CH₃)₂ | |

By substitution of the alkyl or aryl groups introduced as the radical $R^3$ by, for example, halogen atoms, alkyl groups or carboxyl groups, the polarity of the molecule can be influenced. The compound becomes more lipophilic as a result of the introduction of fluorine atoms and is therefore more easily absorbed. Examples of compounds of this type are shown in table 5. In this case, the group $R^3$ was varied for a specific active compound. A variation of this type can also be carried out without problems for other radicals $R^1$ and $R^4$.

TABLE 5

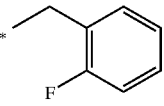

| Number | R³ | B | C | FAB |
|---|---|---|---|---|
| 48 | 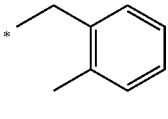 2-F-benzyl | H | H | |
| 49 | 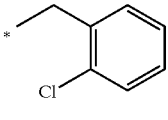 2-methyl-benzyl | H | H | |
| 50 | 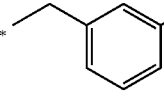 2-Cl-benzyl | H | H | |
| 51 | 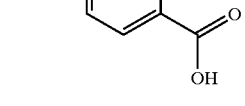 3-Cl-benzyl | H | H | |
| 52 | 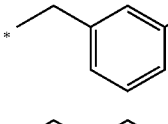 4-COOH-benzyl | H | H | |
| 53 | 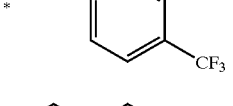 3-methyl-benzyl | H | H | |
| 54 | 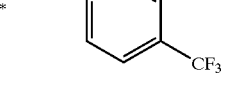 4-CF₃-benzyl | H | H | 582 |
| 55 | 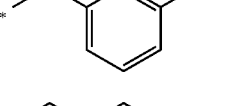 4-CF₃-benzyl | H | H | 582 |
| 56 | 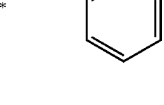 3-OCF₃-benzyl | H | H | |
| 57 | 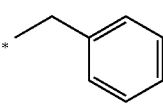 benzyl | H | F | 532 |
| 58 | 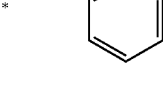 3-CF₃-benzyl | H | F | 600 |
| 59 | 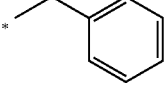 4-CF₃-benzyl | H | F | 600 |
| 60 | 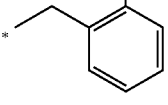 2-CF₃-benzyl | H | H | 582 |
| 61 | 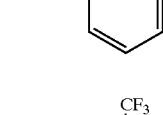 2-CF₃-benzyl | H | F | 600 |
| 62 | 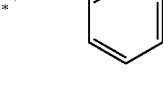 benzyl | F | F | 550 |
| 63 | 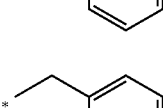 2-CF₃-benzyl | F | F | 618 |
| 64 | 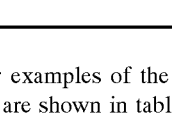 3-CF₃-benzyl | F | F | 618 |
| 65 |  4-CF₃-benzyl | F | F | 618 |

Further examples of the radicals R³ which contain heteroatoms are shown in table 6. The variation of the radical R³ was in this case performed by way of example on a sulfonamide derivative.

TABLE 6

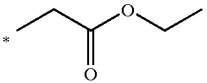

| Number | R³ | FAB |
|---|---|---|
| 66 | 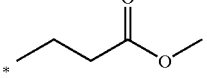 | |
| 67 | 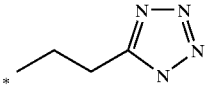 | |
| 68 | 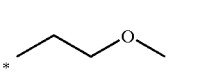 | |
| 69 | 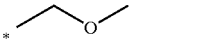 | |
| 70 |  | |
| 71 | 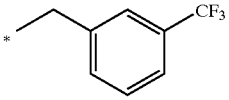 | |

Examples in which the lipophilicity of a part of the compounds was varied are shown in table 7. Here, in a part of the compounds, the radical R³ includes a trifluoromethyl group. Furthermore, in some of the compounds, one or two fluorine atoms were introduced into the biphenyl moiety of the molecule. The variation can be transferred to the other compounds of the formula I without problems.

TABLE 7

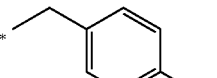

| Number | R³ | B | C | RAB |
|---|---|---|---|---|
| 72 | 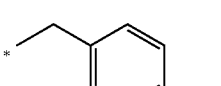 | H | H | |
| 73 | 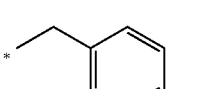 | H | H | |

TABLE 7-continued

| Number | R³ | B | C | RAB |
|---|---|---|---|---|
| 74 | 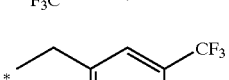 | H | H | |
| 75 | 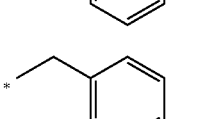 | H | H | |
| 76 | 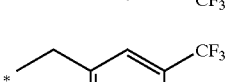 | F | H | |
| 77 | 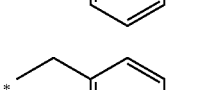 | F | H | |
| 78 | 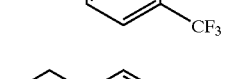 | F | H | |
| 79 | 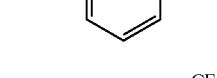 | F | H | 587 |
| 80 | 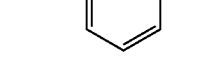 | H | H | 569 |
| 81 | 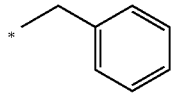 | H | H | 569 |
| 82 | 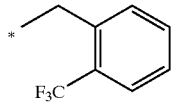 | F | H | 519 |
| 83 | | F | H | 587 |
| 84 | | H | H | 501 |

TABLE 7-continued

Structure: H2N-CH2-[phenyl]-NH-N(R³)-C(O)-NH-[phenyl(B,C)]-[phenyl-SO2CH3]

| Number | R³ | B | C | RAB |
|---|---|---|---|---|
| 85 | 2-(CF3)benzyl* | H | F | 587 |
| 86 | benzyl* | F | F | 537 |
| 87 | 2-(CF3)benzyl* | F | F | 605 |
| 88 | 4-(CF3)benzyl* | F | F | 605 |

Further compounds are shown in table 8.

TABLE 8

Structure: H2N-C(=NOH)-[phenyl]-NH-N(R³)-C(O)-NH-[phenyl(B,C)]-[phenyl-SO2Me]

| Number | R³ | B | C | FAB |
|---|---|---|---|---|
| 94 | 3-(CF3)benzyl* | H | H | 598 |
| 95 | 4-(CF3)benzyl* | H | H | 598 |
| 96 | benzyl* | F | H | 548 |
| 97 | 3-(CF3)benzyl* | F | H | 616 |
| 98 | 4-(CF3)benzyl* | F | H | 616 |
| 99 | 2-(CF3)benzyl* | H | H | 598 |
| 100 | 2-(CF3)benzyl* | F | H | 616 |
| 101 | benzyl* | F | F | 566 |
| 102 | 2-(CF3)benzyl* | F | F | 634 |
| 103 | 3-(CF3)benzyl* | F | F | 634 |
| 104 | 4-(CF3)benzyl* | F | F | 634 |

The structural elements of the compounds according to the invention shown above with the aid of selected compounds can be combined arbitrarily. The compounds can thereby be tailored to the intended therapeutic use.

The compounds of the formula I can be prepared by processes known per se. Some exemplary synthesis routes are presented below.

The synthesis of the molecular structure is explained with the aid of scheme 1.

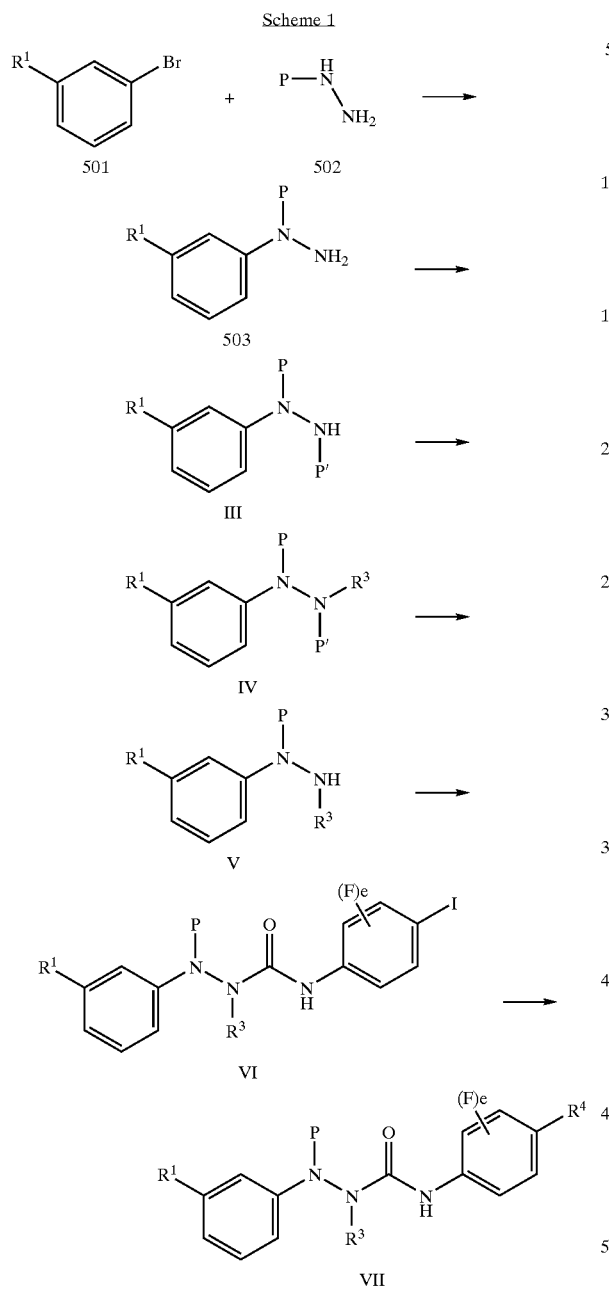

The synthesis starts from the bromobenzene derivative 501. The radical $R^1$ is preferably a group which can be converted into an amidino group at a later point in time in the synthesis. Appropriate structural elements are presented further below. The bromine forms the leaving group for the reaction with the protected hydrazine derivative 502 (Wang Z. et al. Tetrahedron Lett. 1999, 40, 3543–3546). The bromine atom can therefore also be replaced by other suitable leaving groups, for example other halides or sulfonates. The hydrazine derivative 502 has a protective group P. The protective groups used can be customary protective groups for amino groups. A particularly suitable protective group is the BOC protective group. The protected phenylhydrazine derivative 503 is obtained by reaction of the compounds 501 and 502. The free $NH_2$ group is protected in the next reaction step by the protective group P'. The intermediate III is obtained. If possible, the protective groups P and P' are chosen differently in order to make possible selective deprotection of the two nitrogen atoms. The protective group P' used can, as explained above, be the protective groups for amino groups known to the person skilled in the art. Next, the introduction of the radical $R^3$ is carried out, in which, for example, the compound III is reacted with an alkyl halide to give the compound IV. Compound IV is then selectively deprotected on the terminal nitrogen with obtainment of the compound V. By reaction with optionally F substituted iodophenyl isocyanate, the compound VI is obtained. The iodine atom in compound VI can be substituted, whereby the radical $R^4$ can be introduced into the molecule. Compound VII is obtained. The radical $R^4$ is present here in suitably protected form. Examples are illustrated further below. Together with the radicals $R^1$, P and $R^4$, the compound VII in general additionally contains protected structural elements. The removal of the protective group P is carried out according to customary processes, for example using acid.

Scheme 2 shows suitable radicals $R^1$, which remain unchanged in the reaction steps presented above and can then be released starting from compound VII. For reasons of clarity, only the phenyl group having the radical $R^1$ is shown in scheme 2.

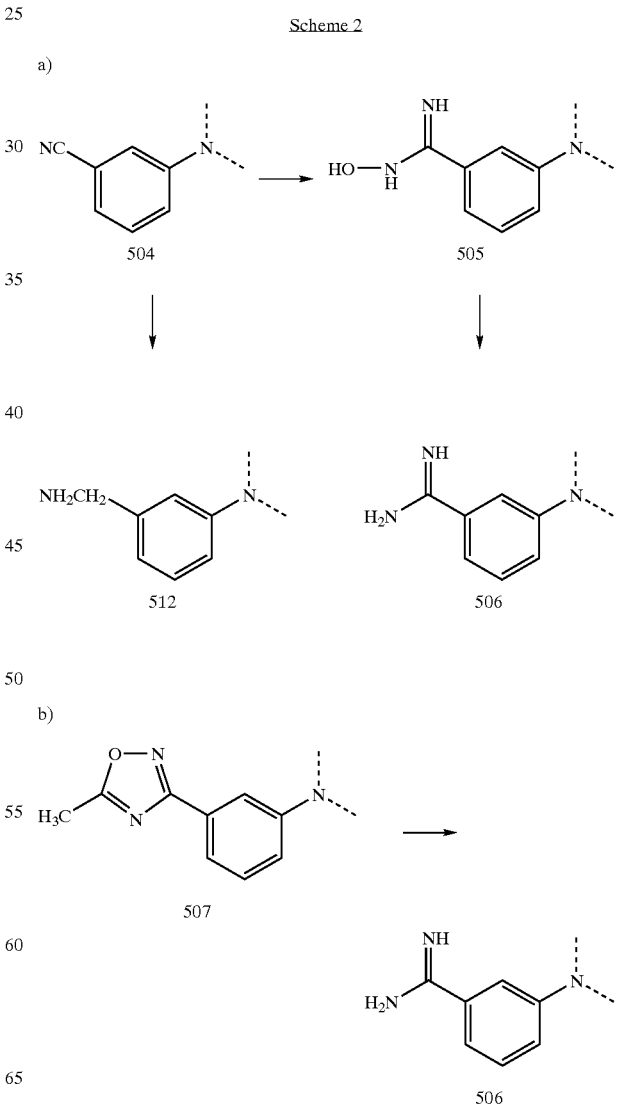

The first possibility consists in the introduction of a nitrile group. This can be converted into the hydroxyamidino group (505) using hydroxylammonium chloride and triethylamine. These compounds can already be used as prodrugs. The amidino group (506) is released by reduction with Raney nickel under a hydrogen atmosphere. The aminomethyl derivative (512) is likewise formed from the nitrile (504) by reduction.

A further possibility is shown under b). This group (507) can likewise be converted into the amidino group (506) using Raney nickel and hydrogen.

In scheme 3, possibilities are presented which allow the introduction of a sulfonamide group (a) and of a methylsulfonyl group (b). Here too, for reasons of clarity only the essential molecular entity ($R^3$) is shown.

Scheme 3 a)

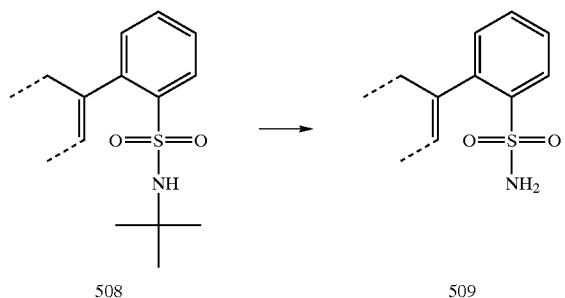

508          509 b)

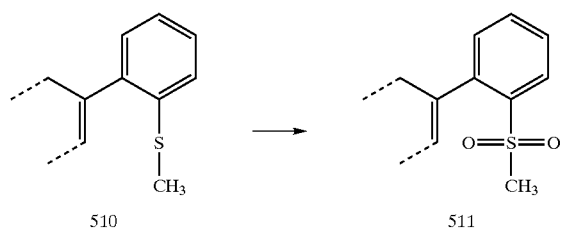

510          511

For the protection of sulfonamides, the amino group is suitably protected. Under (a), the nitrogen, for example, is protected with a tert-butyl group. The removal of the group is carried out using acid, e.g. trifluoroacetic acid.

To introduce the methylsulfonyl group, the corresponding methylthio compound (510) is used as a starting compound. Starting from the corresponding compound VII, the methylthio group is oxidized to the methylsulfonyl compound 511, for example, using sodium perborate trihydrate in acetic acid.

The reaction schemes indicated above can be varied by the person skilled in the art without problems. For example, other leaving or protective groups can be employed. If racemic mixtures are obtained in the reactions, diastereomers can be formed from these in the customary manner by reaction with an optically active resolving agent, and are then separated according to customary processes. A chromatographic resolution of enantiomers with the aid of an optically active resolving agent (e.g. dinitrobenzylphenylglycine, cellulose triacetate or other derivatives of carbohydrates or chirally derivatized methacrylate polymers attached to kieselguhr) is also advantageous.

The invention further relates to the use of the compounds of the formula I and/or their physiologically acceptable salts for the production of pharmaceutical preparations, in particular by a non chemical route. In this connection, they can be brought into a suitable dose form, together with at least one solid, liquid and/or semiliquid vehicle or excipient and if appropriate in combination with one or more further active compounds.

The invention further relates to pharmaceutical preparations comprising at least one compound of the formula I and/or one of its physiologically acceptable salts.

These preparations can be used as medicaments in human or veterinary medicine. Possible vehicles are organic or inorganic substances which are suitable for enteral (e.g. oral) or parenteral administration or topical application and do not react with the novel compounds, for example water, vegetable oils, benzyl alcohols, alkylene glycols, polyethylene glycols, glyceryl triacetate, gelatin, carbohydrates such as lactose or starch, magnesium stearate, talc and petroleum jelly. In particular, tablets, pills, coated tablets, capsules, powders, granules, syrups, juices or drops are suitable for oral administration, suppositories are suitable for rectal administration, solutions, preferably oily or aqueous solutions, furthermore suspensions, emulsions or implants, are suitable for parenteral administration, and ointments, creams or powders are suitable for topical application. The novel compounds can also be lyophilized and the lyophilizates obtained used, for example, for the production of injection preparations. The preparations indicated can be sterilized and/or can contain excipients, such as lubricants, preservatives, stabiizers and/or wetting agents, emulsifiers, salts for influencing the osmotic pressure, buffer substances, colorants, flavorings and/or one or more further active compounds, e.g. one or more vitamins.

The compounds of the formula I and their physiologically acceptable salts can be used in the control and prevention of thromboembolic disorders such as thrombosis, myocardial infarct, arteriosclerosis, inflammation, apoplexy, angina pectoris, restenosis after angioplasty and intermittent claudication.

As a rule, the substances according to the invention are preferably administered here in doses of between 1 and 500 mg, in particular between 5 and 100 mg, per dose unit. The daily dose is preferably between approximately 0.02 and 10 mg/kg of body weight. The specific dose for each patient depends, however, on various factors, for example on the efficacy of the specific compound employed, on the age, body weight, general state of health, sex, on the diet, on the time and route of administration, and on the excretion rate, pharmaceutical combination and severity of the particular disorder to which the therapy relates. Oral administration is preferred.

The invention is illustrated in greater detail with the aid of examples.
EXAMPLE A
Synthesis 4'-[3-(3-amidinophenyl)-2-propylcarbazoylamino]biphenyl-2-sulfonamide 1
The synthesis is shown in scheme 4.
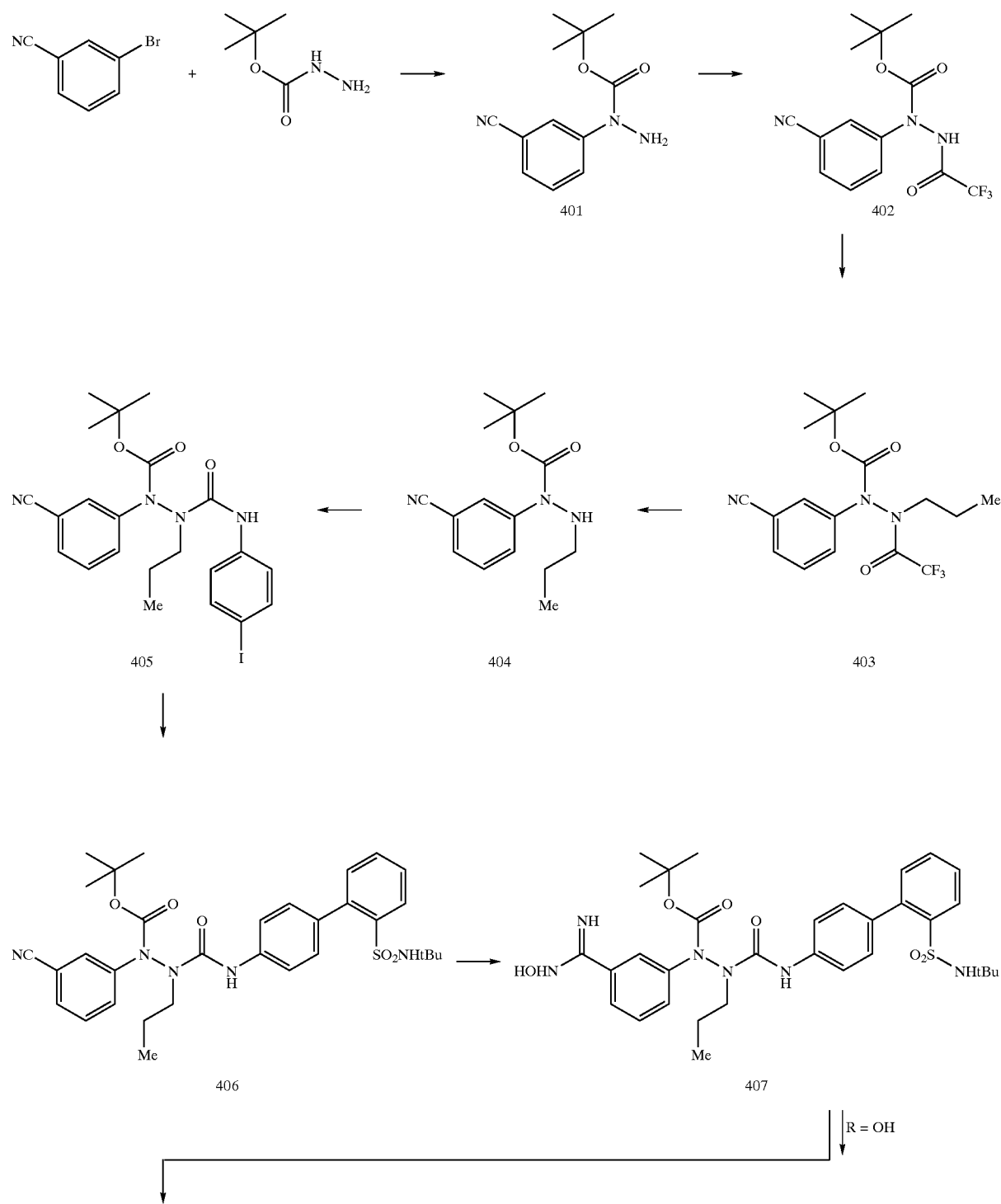

-continued

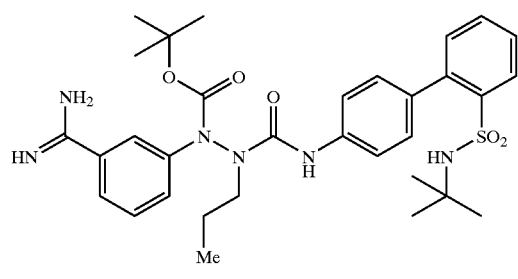

408

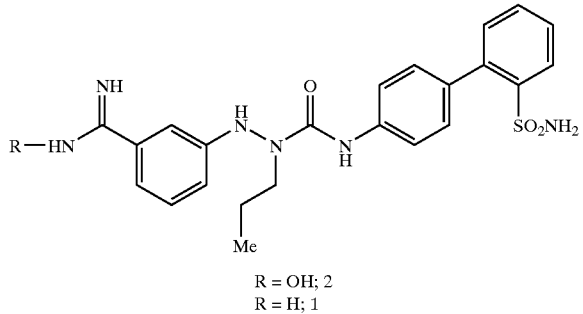

R = OH; 2
R = H; 1 tert-Butyl 2-(3-cyanophenyl)carbazate 401

50.0 g (0.275 mol) of 3-bromobenzonitrile in 400 ml of THF are treated under a nitrogen atmosphere with 36.345 g (0.275 mol) of tert-butyl carbazate, 89.6 g (0.275 mol) of cesium carbonate, 1.581 g (0.003 mol) of bis (dibenzylideneacetone)palladium and 4.602 g (0.008 mol) of 1,1'-bis(diphenylphosphino)ferrocene and the mixture is then stirred at 110° C. for 18 h. After cooling and customary work-up, 15.8 g (24.7%) of 401 are obtained as an oil; MS(FAB)=234. [The reaction is carried out analogously to a procedure of Wang et al. Tetrahedron Lett. 1999, 40, 3543].

tert-Butyl 2-(3-cyanophenyl)-3-(2,2,2-trifluoroacetyl) carbazate 402

10.7 g (46 mmol) of 401 are treated with 9.54 ml (68.8 mmol) of triethylamine in 200 ml of THF. 7.02 ml (50.46 mmol) of trifluoroacetic anhydride are slowly added dropwise with cooling to 5° C. After stirring for 6 h, the mixture is worked up in the customary manner and 14.3 g (94.7%) of 402 are thus obtained as an oil, which is employed directly in stage 3.

tert-Butyl 2-(3-cyanophenyl)-3-propyl-3-(2,2,2-trifluoroacetyl)carbazate 403

5.0 g (15.19 mmol) of the crude product 402 are treated with 7.42 g (22.77 mmol) of cesium carbonate in 100 ml of DMF under a nitrogen atmosphere. After 30 min, 3.87 ml (22.77 mmol) of 1-iodopropane are slowly added dropwise and the mixture is then stirred at RT for 18 h. After customary work-up, 5.64 g (100%) of 403 are thus obtained as an oil, which is employed directly in stage 4.

tert-Butyl 2-(3-cyanophenyl)-3-propylcarbazate 404

5.64 g (15.187 mmol) of crude product 403 are dissolved in 100 ml of methanol and treated at RT with 10 ml of completely deionized water and 1.08 g (45.24 mmol) of lithium hydroxide. The reaction mixture is then stirred for 5 h. After customary work-up, 2.67 g (63.8%) of 404 are thus obtained as an oil; MS(FAB)=276.

tert-Butyl 2-(3-cyanophenyl)-3-(4-iodophenylaminocarbonyl)-3-propylcarbazate 405

2.0 g (7.273 mmol) of 404 are stirred at RT for 1.5 h in 5.0 ml of pyridine with 1.78 g (7.265 mmol) of 4-iodophenyl isocyanate. After customary work-up, 3.2 g (84.7%) of 405 are thus obtained as crystals having a melting point of 184–185° C.; MS(FAB)=521.

4'-[3-tert-Butoxycarbonyl-3-(3-cyanophenyl)-2-propylcarbazoylamino]-N-tert-butylbiphenyl-2-sulfonamide 406

1.5 g (2.883 mmol) of 405 and 1.112 g (4.324 mmol) of 2-(t-butylamino-sulfonyl)phenylboronic acid are dissolved in 100 ml of ethylene glycol dimethyl ether, treated with 63 mg (0.086 mmol) of $PdCl_2(dppf)$ and 20.0 ml of 2N sodium carbonate solution and then stirred at 110° C. under a nitrogen atomsphere for 3 h. After customary work-up, 1.32 g (75.6%) of 406 are thus obtained as crystals having a melting point of 173–174° C.; MS(FAB)=606.

4'-[3-tert-Butoxycarbonyl-3-[3-($N^1$-hydroxyamidino) phenyl]-2-propylcarbazoylamino]-N-tert-butylbiphenyl-2-sulfonamide 407

A suspension of 1.0 g (1.651 mmol) of 406 in 25.0 ml of ethanol are treated with 0.459 g (6.604 mmol) of hydroxylammonium chloride and 0.916 ml (6.604 mmol) of triethylamine and the mixture is stirred under reflux for 5 h. After customary work-up, 1.05 g (99.6%) of 407 are thus obtained as crystals having a melting point of 218–219° C.; MS(FAB)=639.

4'-[3-(3-Amidinophenyl)-3-tert-butoxycarbonyl-2-propylcarbazoylamino]-N-tert-butylbiphenyl-2-sulfonamide 408

0.7 g (1.096 mmol) of 407 is dissolved in 10.0 ml of methanol, treated with 0.25 ml of acetic acid and 0.3 g of water-moist Raney nickel and the mixture is stirred under an $H_2$ atmosphere for 18 h. After customary work-up, 0.62 g (90.8%) of 408 is thus obtained as crystals having a melting point of >300° C.; MS(FAB)=623.

4'-[3-(3-(N-2-Hydroxyamidino)phenyl)-2-propylcarbazoylamino]biphenyl-2-sulfonamide (2)

0.2 g (0.313 mmol) of 407 is dissolved in 5.0 ml of trifluoroacetic acid and the solution is stirred at 5° C. for 18 h. After customary work-up, 0.15 g (99.3%) of 2 is thus obtained as crystals having a melting point of 163–164° C.; MS(FAB)=483.

4'-[3-(3-Amidinophenyl)-2-propylcarbazoylamino] biphenyl-2-sulfonamide (1)

0.5 g (0.803 mmol) of 408 is dissolved in 5.0 ml of trifluoroacetic acid and stirred at 5C for 18 h. After customary work-up, 0.15 g (99.3%) of 1 is thus obtained as crystals having a melting point of 215–216° C.; MS(FAB)=467.

EXAMPLE B

Synthesis of 1-(3-amidinophenly)-4-(2'-methylsulfonylbiphenyl-4-ylamino)-2-propylsemicarbazide 15

The synthesis is shown in scheme 5:

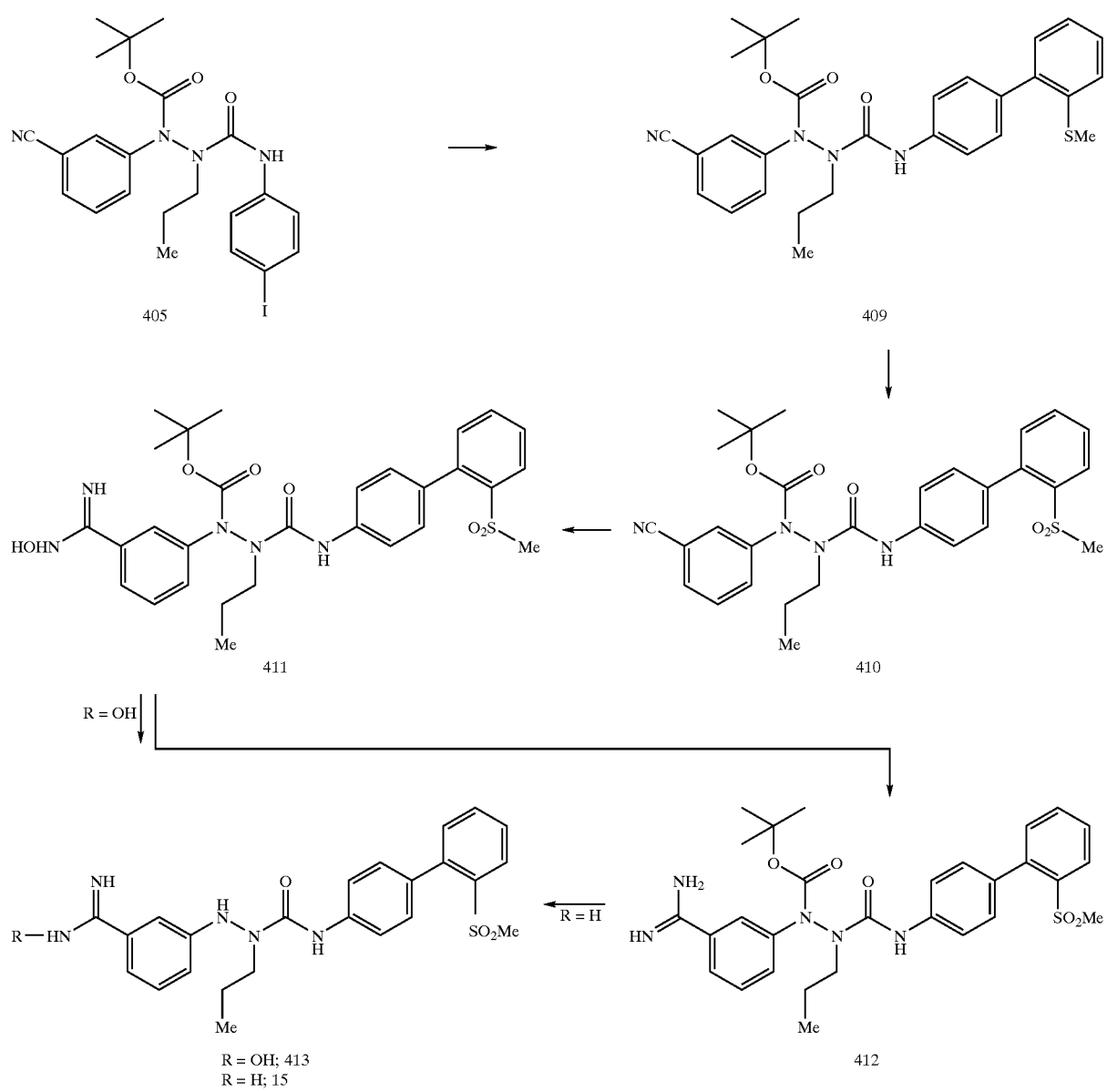

tert-Butyl 2-(3-cyanophenyl)-3-(2'-methylthiobiphenyl-4-ylaminocarbonyl)-3-propylcarbazate 409

1.5 g (2.883 mmol) of 405 and 0.968 g (5.766 mmol) of 2-(methylthio)-phenylboronic acid are dissolved in 100 ml of ethylene glycol dimethyl ether, treated with 63 mg (0.086 mmol) of PdCl$_2$(dppf) and 20.0 ml of 2N sodium carbonate solution and then stirred at 110° C. under a nitrogen atmosphere for 3 h. After customary work-up, 1.28 g (75.9%) of 409 are thus obtained as crystals having a melting point of 184–185° C.; MS(FAB)=517.

tert-Butyl 2-(3-cyanophenyl)-3-(2'-methylsulfonylbiphenyl-4-ylaminocarbonyl)-3-propylcarbazate 410

0.8 g (1.548 mmol) of 409 is suspended in 15 ml of acetic acid with 1.433 g (9.312 mmol) of sodium perborate trihydrate and the mixture is stirred at 60° C. for 18 h. After customary work-up, 0.65 g (76.5%) of 410 is thus obtained as crystals having a melting point of 194–195° C.; MS(FAB)=549.

tert-Butyl 2-[3-(N$^1$-hydroxyamidino) phenyl]-3-(2'-methylsulfonylbiphenyl-4-ylaminocarbonyl)-3-propylcarbazate 411

A solution of 0.6 g (1.094 mmol) of 410 is dissolved in 25 ml of ethanol, treated with 0.304 g (4.376 mmol) of hydroxylammonium chloride and 0.608 ml of (4.376 mmol) of triethylamine and then stirred under reflux for 18 h. After customary work-up, 0.11 g (17.3%) of 411 is thus obtained as crystals having a melting point of 187–188° C.; MS(FAB)=582.

1-(3-N²-Hydroxyamidinophenyl)-4-(2'-methylsulfonylbiphenyl-4-ylamino)-2-propylsemicarbazide 413

50.0 mg (0.086 mmol) of 411 are dissolved in 1.0 ml of 4N HCl in dioxane. and the solution is stirred at RT for 18 h. After customary work-up, 0.11 g (17.3%) of 413 is thus obtained as crystals having a melting point of 195–196° C.; MS(FAB)=482.

tert-Butyl 2-(3-amidinophenyl)-3-(2'-methylsulfonylbiphenyl4-ylaminocarbonyl)-3-propylcarbazate 412

0.2 g (0.344 mmol) of 411 is dissolved in 5.0 ml of methanol, treated with 0.1 ml of acetic acid and 0.1 g of water-moist Raney nickel and the mixture is stirred under an H₂ atmosphere for 18 h. After customary work-up, 0.19 g (100%) of 412 is thus obtained as crystals having a melting point of >300° C.; MS(FAB)=566.

1-(3-Amidinophenyl)-4-(2'-methylsulfonylbiphenyl-4-ylamino)-2-propylsemicarbazide 15

0.2 g (0.354 mmol) of 412 is dissolved in 10 ml of 4N HCl in dioxane and the mixture is stirred at RT for 18 h. After customary work-up, 0.13 g (76.9%) of 15 is thus obtained as crystals having a melting point of >300° C.; MS(FAB)=466.

What is claimed is:

1. A semicarbazide of formula I,

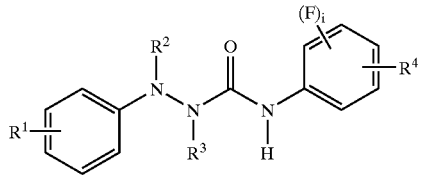

wherein:
R¹ is —(CH₂)ₙ—NH₂, —CON=C(NH₂)₂, —NHC(=NH)—NH₂ or —C(=NH)—NH₂, which is optionally monosubstituted by —OH, —OCOOA, —OCOO(CH₂)ₙN(A)₂, —OCOO(CH₂)ₘ—Het, —CO—C(A)₂—R⁵, —COOA, —COSA, —COOAr, —COOAr',

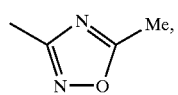 or by 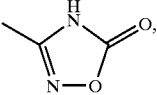

R² is H, or COOA,
R³ is unbranched, branched or cyclic alkyl having 1–20 C atoms, in which one or two CH₂ groups are optionally each independently of one another replaced by an O or S atom, or is Ar, Ar', X or Hal,
R⁴ is phenyl monosubstituted by S(O)ₖA, S(O)ₖNHA, CF₃, COOA, CH₂NHA, CN or OA,
R⁵ is —CHal₃, —O(C=O)A or

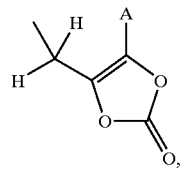

Ar is phenyl or naphthyl, which is unsubstituted or mono-, di- or trisubstituted by A, OH, OA, NH₂, NHA, NA₂, NO₂, CF₃, CN, Hal, NHCOA, COOA, CONH₂, CONHA, CONA₂, S(O)ₙA, S(O)ₙNH₂, S(O)ₙNHA, or S(O)ₙNA₂, Ar' is —(CH₂)ₙ—Ar,
Het is a mono- or binuclear, saturated, unsaturated or aromatic heterocycle having 1 to 4 N, O and/or S atoms, bonded via N or C, which is optionally unsubstituted or substituted by A,
A is H, unbranched, branched or cyclic alkyl having 1–20 C atoms,
X is —(CH₂)ₙ—Y,
Y is COOA, or

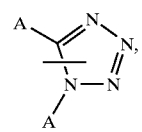

Hal is F, Cl, Br or I,
n is 1, 2, 3, 4, 5 or 6,
m is 0 or 1,
k is 0, 1 or 2, and
i is 0, 1, 2, 3 or 4,
or a pharmaceutically acceptable salt or solvate thereof.

2. A semicarbazide as claimed in claim 1, which is of formula II

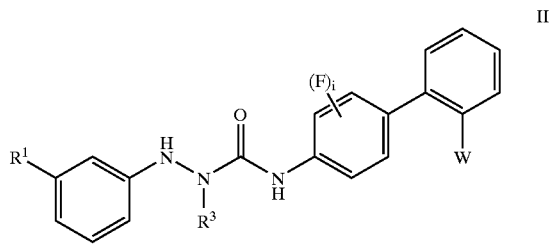

wherein R¹, R³, A and k have the meaning indicated in claim 1 and W is S(O)ₖA, S(O)ₖNHA, CF₃, COOA, CH₂NHA, CN or OA, and i is 0, 1 or 2.

3. A compound which is:
4'-[3-(3-amidinophenyl)-2-propylcarbazoylamino]biphenyl-2-sulfonamide (1),
4'-[3-(3-(N²-hydroxyamidino)phenyl)-2-propylcarbazoylamino]biphenyl-2-sulfonamide (2),
4'-[3-(3-amidinophenyl)-2-methylcarbazoylamino]biphenyl-2-sulfonamide (3),
1-(3-amidinophenyl)-2-methyl-4-(2'-methylsulfonylbiphenyl-4-yl)semicarbazide (4),
4'-[3-(3-amidinophenyl)-2-ethylcarbazoylamino]biphenyl-2-sulfonamide (5),
1-(3-amidinophenyl)-2-ethyl-4-(2'-methylsulfonylbiphenyl-4-yl)semicarbazide (6),
4'-[3-(3-amidinophenyl)-2-isopropylcarbazoylamino]biphenyl-2-sulfonamide (7),
1-(3-amidinophenyl)-2-isopropyl-4-(2'-methylsulfonylbiphenyl-4-yl)semicarbazide (8),
4'-[3-(3-amidinophenyl)-2-butylcarbazoylamino]biphenyl-2-sulfonamide (9),
1-(3-amidinophenyl)-2-butyl-4-(2'-methylsulfonylbiphenyl-4-yl)semicarbazide (10), 4'-[3-(3-amidinophenyl)-2-isobutylcarbazoylamino] biphenyl-2-sulfonamide (11), 1-(3-amidinophenyl)-2-isobutyl-4-(2'-methylsulfonylbiphenyl-4-yl)semicarbazide (12), 4'-[3-(3-amidinophenyl)-2-pentylcarbazoylamino] biphenyl-2-sulfonamide (13), 1-(3-amidinophenyl)-4-(2'-methylsulfonylbiphenyl-4-ylamino)-2-pentylsemicarbazide (14), 1-(3-amidinophenyl)-4-(2'-methylsulfonylbiphenyl-4-ylamino)-2-propylsemicarbazide (15), 4'-[3-(3-amidinophenyl)-2-(2-butyl)carbazoylamino] biphenyl-2-sulfonamide (16), 1-(3-amidinophenyl)-2-(2-butyl)-4-(2'-methylsulfonylbiphenyl-4-yl)semicarbazide (17), 4'-[3-(3-amidinophenyl)-2-(cyclohexylmethyl) carbazoylamino]biphenyl-2-sulfonamide (18), 1-(3-amidinophenyl)-2-(cyclohexylmethyl)-4-(2'-methylsulfonylbiphenyl-4-yl)-semicarbazide (19), 4'-[3-(3-amidinophenyl)-2-benzylcarbazoylamino] biphenyl-2-sulfonamide (20), 1-(3-amidinophenyl)-2-benzyl-4-(2'-methylsulfonylbiphenyl-4-yl)semicarbazide (21), 1-(3-N-$^2$-hydroxyamidinophenyl)-2-benzyl-4-(2'-methylsulfonylbiphenyl-4-yl)-semicarbazide (22), 4'-[3-(3-amidinophenyl)-2-phenylcarbazoylamino] biphenyl-2-sulfonamide (23), 1-(3-amidinophenyl)-4-(2'-methylsulfonylbiphenyl-4-yl)-2-phenylsemicarbazide (24), methyl N-[3-[2-benzyl-4-(2'-methylsulfonylbiphenyl-4-yl)semicarbazido]phenyl-(iminomethyl)]carbamate (25), 2,2,2-trichloroethyl N-[3-[2-benzyl-4-(2'-methylsulfonylbiphenyl-4-yl)-semicarbazido]phenyl (iminomethyl)]carbamate (26), S-ethyl N-[3-[2-benzyl-4-(2'-methylsulfonylbiphenyl-4-yl)semicarbazido]-phenyl(iminomethyl)] thiocarbamate (27), 4-methoxybenzyl N-[3-[2-benzyl-4-(2'-methylsulfonylbiphenyl-4-yl)semicarbazido]-phenyl (iminomethyl)]carbamate (28), ethyl N-[3-[2-benzyl-4-(2'-methylsulfonylbiphenyl-4-yl) semicarbazido]-phenyl(iminomethyl)]carbamate (29), propyl N-[3-[2-benzyl-4-(2'-methylsulfonylbiphenyl-4-yl)semicarbazido]-phenyl(iminomethyl)]carbamate (30), butyl N-[3-[2-benzyl-4-(2'-methylsulfonylbiphenyl-4-yl) semicarbazido]-phenyl(iminomethyl)]carbamate (31), isopropyl N-[3-[2-benzyl-4-(2'-methylsulfonylbiphenyl-4-yl)semicarbazido]phenyl(iminomethyl)]carbamate (32), isobutyl N-[3-[2-benzyl4-(2'-methylsulfonylbiphenyl-4-yl)semicarbazido]-phenyl(iminomethyl)]carbamate (33), allyl N-[3-[2-benzyl-4-(2'-methylsulfonylbiphenyl-4-yl) semicarbazido]-phenyl(iminomethyl)]carbamate (34), phenyl N-[3-[2-benzyl-4-(2'-methylsulfonylbiphenyl-4-yl)semicarbazido]-phenyl(iminomethyl)]carbamate (35), 2-fluorophenyl N-[3-[2-benzyl-4-(2'-methylsulfonylbiphenyl-4-yl)semicarbazido]phenyl (iminomethyl)]carbamate (36), 2-benzyl-1-[3-(N$^1$-(methylcarboxy)amidino)phenyl]-4-(2'-methylsulfonylbiphenyl-4-yl)semicarbazide (37), 2-benzyl-4-(2'-methylsulfonylbiphenyl-4-yl)-1-[3-(N$^1$-(phenylcarboxy)$^1$midino)phenyl]semicarbazide (38), 2-benzyl-1-[3-(N$^1$-(isobutylcarboxy)amidino)phenyl]-4-(2'-methylsulfonylbiphenyl-4-yl)semicarbazide (39), 2-benzyl-1-[3-[N$^1$-(2-methylcarboxy-2-propoxycarbonyl)amidino]phenyl]-4-(2'-methylsulfonylbiphenyl-4-yl)semicarbazide (40), 2-benzyl-1-[3-[N$^1$-(1-(methylcarboxy)ethoxycarbonyl) amidino]phenyl]-4-(2'-methylsulfonylbiphenyl-4-yl) semicarbazide (41), 1-methyl-4-piperidinyl N-[3-[2-benzyl-4-(2'-methylsulfonylbiphenyl-4-yl)semicarbazido]phenyl (iminomethyl)]carbamate (42), 2-(4-pyridyl)ethyl N-[3-[2-benzyl-4-(2'-methylsulfonylbiphenyl-4-yl)semicarbazido]phenyl (iminomethyl)]carbamate (43), 5-methyl-2-oxo-1,3-dioxol-4-ylmethyl N-[3-[2-benzyl-4-(2'-methylsulfonylbiphenyl-4-yl)semicarbazido] phenyl(iminomethyl)]carbamate (44), 2-(3-pyridyl)ethyl N-[3-[2-benzyl-4-(2'-methylsulfonylbiphenyl-4-yl)semicarbazido]phenyl (iminomethyl)]carbamate (45), 2-(N,N-diethylamino)ethyl N-[3-[2-benzyl-4-(2'-methylsulfonylbiphenyl-4-yl)semicarbazido]phenyl (iminomethyl)]carbamate (46), 2-(N-morpholinyl)ethyl N-[3-[2-benzyl-4-(2'-methylsulfonylbiphenyl-4-yl)semicarbazido]phenyl (iminomethyl)]carbamate (47), 1-(3-amidinophenyl)-2-(2-fluorobenzyl)-4-(2'-methylsulfonylbiphenyl-4-yl)semicarbazide (48), 1-(3-amidinophenyl)-2-(2-methylbenzyl)-4-(2'-methylsulfonylbiphenyl-4-yl)semicarbazide (49), 1-(3-amidinophenyl)-2-(2-chlorobenzyl)-4-(2'-methylsulfonylbiphenyl-4-yl)semicarbazide (50), 1-(3-amidinophenyl)-2-(3-chlorobenzyl)-4-(2'-methylsulfonylbiphenyl-4-yl)semicarbazide (51), 4-[1-(3-amidinophenylamino)-3-(2'-methylsulfonylbiphenyl-4-yl)ureidomethyl]-benzoic acid (52), 1-(3-amidinophenyl)-2-(3-methylbenzyl)-4-(2'-methylsulfonylbiphenyl-4-yl)semicarbazide (53), 1-(3-amidinophenyl)-4-(2'-methylsulfonylbiphenyl-4-yl)-2-(3-trifluoromethyl -benzyl)semicarbazide (54), 1-(3-amidinophenyl)-4-(2'-methylsulfonylbiphenyl-4-yl)-2-(4-trifluoromethyl -benzyl)semicarbazide (55), 1-(3-amidinophenyl)-4-(2'-methylsulfonylbiphenyl-4-yl)-2-(3-trifluoromethoxy benzyl)semicarbazide (56), 1-(3-amidinophenyl)-2-benzyl-4-(2'-methylsulfonyl-3-fluor-biphenyl-4-yl)-semicarbazide (57), 1-(3-amidinophenyl)-2-(3-trifluormethylbenzyl)-4-(2'-methylsulfonyl-3-fluor-biphenyl-4-yl)-semicarbazide (58), 1-(3-amidinophenyl)-2-(4-trifluormethylbenzyl)-4-(2'-methylsulfonyl-3-fluor-biphenyl-4-yl)-semicarbazide (59), 1-(3-amidinophenyl)-2-(2-trifluormethylbenzyl)-4-(2'-methylsulfonylbiphenyl-4-yl)-semicarbazide (60), 1-(3-amidinophenyl)-2-(2-trifluormethylbenzyl)-4-(2'-methylsulfonyl-3-fluor-biphenyl-4-yl)-semicarbazide (61), 1-(3-amidinophenyl)-2-benzyl-4-(2'-methylsulfonyl-3,5-difluor-biphenyl-4-yl)-semicarbazide (62), 1-(3-amidinophenyl)-2-(2-trifluormethylbenzyl)-4-(2'-methylsulfonyl-3,5-difluor-biphenyl-4-yl)-semicarbazide (63), 1-(3-amidinophenyl)-2-(3-trifluormethylbenzyl)-4-(2'-methylsulfonyl-3,5-difluor-biphenyl-4-yl)-semicarbazide (64), 1-(3-amidinophenyl)-2-(4-trifluormethylbenzyl)-4-(2'-methylsulfonyl-3,5-difluor-biphenyl-4-yl)-semicarbazide (65), ethyl 2-[1-(3-amidinophenylamino)-3-(2'-sulfamoylbiphenyl-4-yl)ureido]-acetate (66), ethyl 3-[1-(3-amidinophenylamino)-3-(2'-sulfamoylbiphenyl-4-yl)ureido]-propionate (67), 4'-[3-(3-amidinophenyl)-2-[2-(1-methyltetrazol-5-yl)ethyl]carbazoylamino]-biphenyl-2-sulfonamide (68), 4'-[3-(3-amidinophenyl)-2-(2-methoxyethyl)carbazoylamino]biphenyl-2-sulfonamide (69), 4'-[3-(3-amidinophenyl)-2-(methoxymethyl)carbazoylamino]biphenyl-2-sulfonamide (70), 4'-[3-(3-amidinophenyl)-2-(4-methoxybutyl)carbazoylamino]biphenyl-2-sulfonamide (71), 1-(3-aminomethylphenyl)-2-benzyl-4-(2'-methylsulfonylbiphenyl-4-yl)semicarbazide (72), 1-(3-aminomethylphenyl)-4-(2'-methylsulfonylbiphenyl-4-yl)-2-(2-trifluoro-methylbenzyl)semicarbazide (73), 1-(3-aminomethylphenyl)-4-(2'-methylsulfonylbiphenyl-4-yl)-2-(3-trifluoro-methylbenzyl)semicarbazide (74), 1-(3-aminomethylphenyl)-4-(2'-methylsulfonylbiphenyl-4-yl)-2-(4-trifluoro-methylbenzyl)semicarbazide (75), 1-(3-aminomethylphenyl)-2-benzyl-4-(3-fluoro-2'-methylsulfonylbiphenyl-4-yl)semicarbazide (76), 1-(3-aminomethylphenyl)-4-(3-fluoro-2'-methylsulfonylbiphenyl-4-yl)-2-(2-trifluoromethylbenzyl)semicarbazide (77), 1-(3-aminomethylphenyl)-4-(3-fluoro-2'-methylsulfonylbiphenyl-4-yl)-2-(3-trifluoromethylbenzyl)semicarbazide (78), 1-(3-aminomethylphenyl)-4-(3-fluoro-2'-methylsulfonylbiphenyl-4-yl)-2-(4-trifluoromethylbenzyl)semicarbazide (79), 1-(3-aminomethylphenyl)-2-(3-trifluoromethylbenzyl)-4-(2'-methylsulfonylbiphenyl-4-yl)-semicarbazide (80), 1-(3-aminomethylphenyl)-2-(4-trifluoromethylbenzyl)-4-(2'-methylsulfonylbiphenyl-4-yl)-semicarbazide (81), 1-(3-aminomethylphenyl)-2-benzyl-4-(2'-methylsulfonyl-3-fluoro-biphenyl-4-yl)-semicarbazide (82), 1-(3-aminomethylphenyl)-2-(3-trifluoromethylbenzyl)-4-(2'-methylsulfonyl-3-fluoro-biphenyl-4-yl)-semicarbazide (83), 1-(3-aminomethylphenyl)-2-benzyl-4-(2'-methylsulfonylbiphenyl-4-yl)-semicarbazide (84), 1-(3-aminomethylphenyl)-2-(2-trifluoromethylbenzyl)-4-(2'-methylsulfonyl-3-fluoro-biphenyl-4-yl)-semicarbazide (85), 1-(3-aminomethylphenyl)-2-benzyl-4-(2'-methylsulfonyl-3,5-difluoro-biphenyl-4-yl)-semicarbazide (86), 1-(3-aminomethylphenyl)-2-(2-trifluoromethylbenzyl)-4-(2'-methylsulfony-3,5-difluoro-biphenyl-4-yl)-semicarbazide (87), 1-(3-aminomethylphenyl)-2-(4-trifluoromethylbenzyl)-4-(2'-methylsulfonyl-3,5-difluoro-biphenyl-4-yl)-semicarbazide (88), 2-Benzyl-1-[3-(N$^1$-methoxy)-amidino)-phenyl]4-(2'-methylsulfonylbiphenyl-4-yl) -semicarbazide (89), 2-Benzyl-1-[3-(N1-ethoxy)-amidino)-phenyl]-4-(2'-methylsulfonylbiphenyl-4-yl) -semicarbazide (90), 2-Benzyl-1-[3-(N1-vinyloxy)-amidino)-phenyl]-4-(2'-methylsulfonylbiphenyl-4-yl) -semicarbazide (91), 2-Benzyl-1-[3-(N1-benzyloxy)-amidino)-phenyl]-4-(2'-methylsulfonylbiphenyl-4-yl) -semicarbazide (92), 2-Benzyl-1-[3-(N1-isopropoxy)-amidino)-phenyl]-4-(2'-methylsulfonylbiphenyl-4-yl) -semicarbazide (93), 1-[3-(N-Hydroxyamidino)-phenyl]-2-(3-trifluoromethylbenzyl)-4-(2'-methylsulfonylbiphenyl-4-yl)-semicarbazide (94), 1-[3-(N-Hydroxyamidino)-phenyl]-2-(4-trifluoromethylbenzyl)-4-(2'-methylsulfonylbiphenyl-4-yl)-semicarbazide (95), 1-[3-(N-Hydroxyamidino)-phenyl]-2-benzyl4-(2'-methylsulfonyl-3-fluorobiphenyl-4-yl) -semicarbazide (96), 1-[3-(N-Hydroxyamidino)-phenyl]-2-(3-trifluoromethylbenzyl)-4-(2'-methylsulfonyl-3-fluorobiphenyl4-yl)-semicarbazide (97), 1-[3-(N-Hydroxyamidino)-phenyl]-2-(4-trifluoromethylbenzyl)-4-(2'-methylsulfonyl-3-fluorobiphenyl-4-yl)-semicarbazide (98), 1-[3-(N-Hydroxyamidino)-phenyl]-2-(2-trifluoromethylbenzyl)-4-(2'-methylsulfonylbiphenyl-4-yl)-semicarbazide (99), 1-[3-(N-Hydroxyamidino)-phenyl]-2-(2-trifluoromethylbenzyl)-4-(2'-methylsulfonyl-3-fluorobiphenyl-4-yl)-semicarbazide (100), 1-[3-(N-Hydroxyamidino)-phenyl]-2-benzyl-4-(2'-methylsulfonyl-3,5-difluorobiphenyl-4-yl)-semicarbazide (101), 1-[3-(N-Hydroxyamidino)-phenyl]-2-(2-trifluoromethylbenzyl)-4-(2'-methylsulfonyl-3,5-difluoro-biphenyl-4-yl)-semicarbazide (102), 1-[3-(N-Hydroxyamidino)-phenyl]-2-(3-trifluoromethylbenzyl)-4-(2-methylsulfonyl-3,5-difluoro-biphenyl-4-yl)-semicarbazide (103), or 1-[3-(N-Hydroxyamidino)-phenyl]-2-(4-trifluoromethylbenzyl)-4-(2-methylsulfonyl-3,5-difluoro-biphenyl-4-yl)-semicarbazide (104).

4. A compound of formula III:

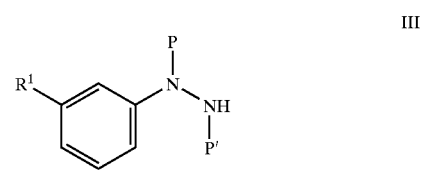

wherein

P and P' are identical or different and are each a protective group for nitrogen, $R^1$ is —$(CH_2)_n$—$NH_2$, —CON=$C(NH_2)_2$, —NHC(=NH)—$NH_2$ or —C(=NH)—$NH_2$, which is optionally monosubstituted by —OH, —OCOOA, —OCOO$(CH_2)_n N(A)_2$, —OCOO$(CH_2)_m$—Het, —CO—$C(A)_2$—$R^5$, —COOA, —COSA, —COOAr, —COOAr',

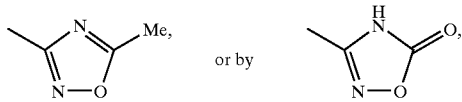 or by 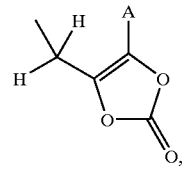

R⁵ is —CHal₃, —O(C=O)A or

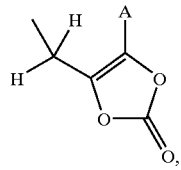

A is H, or an unbranched, branched or cyclic alkyl having 1–20 C atoms,

Ar is phenyl or naphthyl, which is unsubstituted or mono-, di- or trisubstituted by A, OH, OA, $NH_2$, NHA, $NA_2$, $NO_2$, $CF_3$, CN, Hal, NHCOA, COOA, $CONH_2$, CONHA, $CONA_2$, $S(O)_nA$, $S(O)_nNH_2$, $S(O)_nNHA$, or $S(O)_nNA_2$, Ar' is —$(CH_2)_n$—Ar, Het is a mono- or binuclear, saturated, unsaturated or aromatic heterocycle having 1 to 4 N, O and/or S atoms, bonded via N or C, which is optionally unsubstituted or substituted by A, Hal is F, Cl, Br or I, n is 1, 2, 3, 4, 5 or 6, and m is 0 or 1.

5. A compound of formula IV

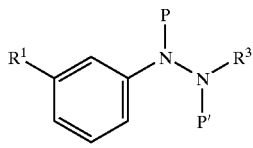

wherein

R¹ is —$(CH_2)_n$—$NH_2$, —CON=C($NH_2$)₂, —NHC(=NH)—$NH_2$ or —C(=NH)—$NH_2$, which is optionally monosubstituted by —OH, —OCOOA, —OCOO$(CH_2)_nN(A)_2$, —OCOO$(CH_2)_m$—Het, —CO—C(A)₂—R⁵, —COOA, —COSA, —COOAr, —COOAr',

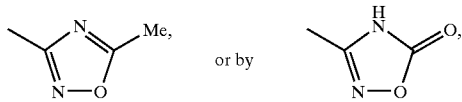 or by

R³ is unbranched, branched or cyclic alkyl having 1–20 C atoms, in which one or two $CH_2$ groups are optionally each independently of one another replaced by an O or S atom, or is Ar, Ar', X or Hal, P and P' are identical or different and are each a protective group for nitrogen, R⁵ is —CHal₃, —O(C=O)A or

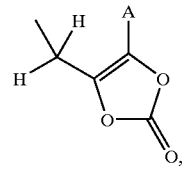

A is H, or an unbranched, branched or cyclic alkyl having 1–20 C atoms,

Ar is phenyl or naphthyl, which is unsubstituted or mono-, di- or trisubstituted by A, OH, OA, $NH_2$, NHA, $NA_2$, $NO_2$, $CF_3$, CN, Hal, NHCOA, COOA, $CONH_2$, CONHA, $CONA_2$, $S(O)_nA$, $S(O)_nNH_2$, $S(O)_nNHA$, or $S(O)_nNA_2$, Ar' is —$(CH_2)_n$—Ar, Het is a mono- or binuclear, saturated, unsaturated or aromatic heterocycle having 1 to 4 N, O and/or S atoms, bonded via N or C, which is optionally unsubstituted or substituted by A, Hal is F, Cl, Br or I, n is 1, 2, 3, 4, 5 or 6, m is 0 or 1, X is —$(CH_2)_n$—Y, and Y is —COOA, or

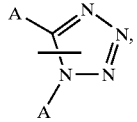

6. A compound of formula V

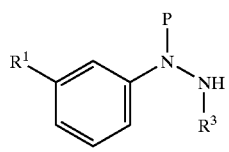

wherein

R¹ is —$(CH_2)_n$—$NH_2$, —CON=C($NH_2$)₂, —NHC(=NH)—$NH_2$ or —C(=NH)—$NH_2$, which is optionally monosubstituted by —OH, —OCOOA, —OCOO$(CH_2)_nN(A)_2$, —OCOO$(CH_2)_m$—Het, —CO—C(A)₂—R⁵, —COOA, —COSA, —COOAr, —COOAr',

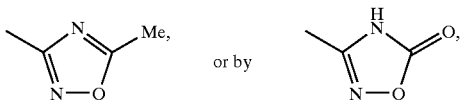 or by

R³ is unbranched, branched or cyclic alkyl having 1–20 C atoms, in which one or two $CH_2$ groups are optionally each independently of one another replaced by an O or S atom, or is Ar, Ar', X or Hal, P is a protective group for nitrogen, R⁵ is —CHal₃, —O(C=O)A or

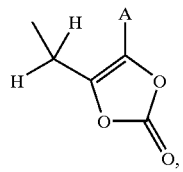

A is H, or an unbranched, branched or cyclic alkyl having 1–20 C atoms,

Ar is phenyl or naphthyl, which is unsubstituted or mono-, di- or trisubstituted by A, OH, OA, NH₂, NHA, NA₂, NO₂, CF₃, CN, Hal, NHCOA, COOA, CONH₂, CONHA, CONA₂, S(O)$_n$A, S(O)$_n$NH₂, S(O)$_n$NHA, or S(O)$_n$NA₂, Ar' is —(CH₂)$_n$—Ar, Het is a mono- or binuclear, saturated, unsaturated or aromatic heterocycle having 1 to 4 N, O and/or S atoms, bonded via N or C, which is optionally unsubstituted or substituted by A, Hal is F, Cl, Br or I, n is 1, 2, 3, 4, 5 or 6, m is 0 or 1, X is —(CH₂)$_n$—Y, and Y is —COOA, or

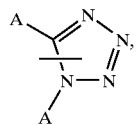

7. A compound of formula VI

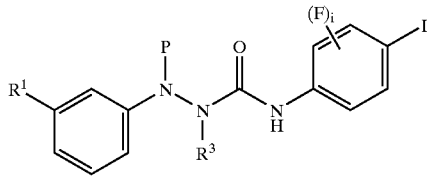

VI wherein

R¹ is —(CH₂)$_n$—NH₂, —CON=C(NH₂)₂, —NHC(=NH)—NH₂ or —C(=NH)—NH₂, which is optionally monosubstituted by —OH, —OCOOA, —OCOO(CH₂)$_n$N(A)₂, —OCOO(CH₂)$_m$—Het, —CO—C(A)₂—R⁵, —COOA, —COSA, —COOAr, —COOAr',

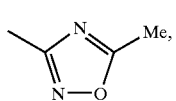 or by 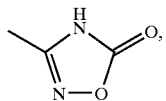

R³ is unbranched, branched or cyclic alkyl having 1–20 C atoms, in which one or two CH₂ groups are optionally each independently of one another replaced by an O or S atom, or is Ar, Ar', X or Hal, P is a protective group for nitrogen, i is 0, 1, 2, 3 or 4, l is iodine, R⁵ is —CHal₃, —O(C=O)A or

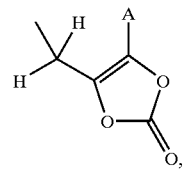

A is H, or an unbranched, branched or cyclic alkyl having 1–20 C atoms,

Ar is phenyl or naphthyl, which is unsubstituted or mono-, di- or trisubstituted by A, OH, OA, NH₂, NHA, NA₂, NO₂, CF₃, CN, Hal, NHCOA, COOA, CONH₂, CONHA, CONA₂, S(O)$_n$A, S(O)$_n$NH₂, S(O)$_n$NHA, or S(O)$_n$NA₂, Ar' is —(CH₂)$_n$—Ar, Het is a mono- or binuclear, saturated, unsaturated or aromatic heterocycle having 1 to 4 N, O and/or S atoms, bonded via N or C, which is optionally unsubstituted or substituted by A, Hal is F, Cl, Br or I, n is 1, 2, 3, 4, 5 or 6, m is 0 or 1, X is —(CH₂)$_n$—Y, and Y is —COOA, or

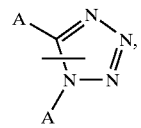

8. A compound of formula VII

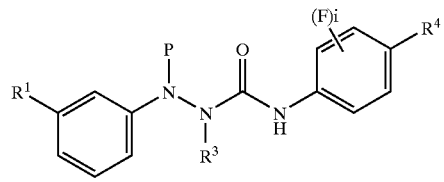

VII wherein

R¹ is —(CH₂)$_n$—NH₂, —CON=C(NH₂)₂, —NHC(=NH)—NH₂ or —C(=NH)—NH₂, which is optionally monosubstituted by —OH, —OCOOA, —OCOO(CH₂)$_n$N(A)₂, —OCOO(CH₂)$_m$—Het, —CO—C(A)₂—R⁵, —COOA, —COSA, —COOAr, —COOAr',

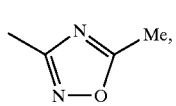 or by 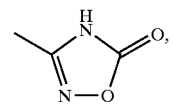

R³ is unbranched, branched or cyclic alkyl having 1–20 C atoms, in which one or two CH₂ groups are optionally each independently of one another replaced by an O or S atom, or is Ar, Ar', X or Hal, P is a protective group for nitrogen, i is 0, 1, 2, 3 or 4, R⁴ is phenyl monosubstituted by S(O)$_k$A, S(O)$_k$NHA, CF$_3$, COOA, CH$_2$NHA, CH$_2$NHA, CN or OA, k is 0, 1 or 2, R⁵ is —CHal$_3$, —O(C=O)A or

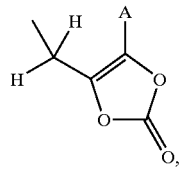

A is H, or an unbranched, branched or cyclic alkyl having 1–20 C atoms,

Ar is phenyl or naphthyl, which is unsubstituted or mono-, di- or trisubstituted by A, OH, OA, NH$_2$, NHA, NA$_2$, NO$_2$, CF$_3$, CN, Hal, NHCOA, COOA, CONH$_2$, CONHA, CONA$_2$, S(O)$_n$A, S(O)$_n$NH$_2$, S(O)$_n$NHA, or S(O)$_n$NA$_2$, Ar' is —(CH$_2$)$_n$—Ar, Het is a mono- or binuclear, saturated, unsaturated or aromatic heterocycle having 1 to 4 N, O and/or S atoms, bonded via N or C, which is optionally unsubstituted or substituted by A, Hal is F, Cl, Br or I, n is 1, 2, 3, 4, 5 or 6, m is 0 or 1, X is —(CH$_2$)$_n$—Y, and Y is —COOA, or

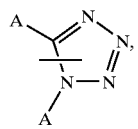

9. A process for preparing a compound of formula I, comprising at least one of the reaction steps a, b, c, or d, a) converting a compound formula III to a compounds of formula IV,

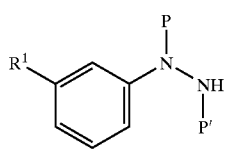

wherein

P and P' are identical or different and are each a protective group for nitrogen, R¹ is —(CH$_2$)$_n$—NH$_2$, —CON=C(NH$_2$)$_2$, —NHC(=NH)—NH$_2$ or —C(=NH)—NH$_2$, which is optionally monosubstituted by —OH, —OCOOA, —OCOO(CH$_2$)$_n$N(A)$_2$, —OCOO(CH$_2$)$_m$—Het, —CO—C(A)$_2$—R⁵, —COOA, —COSA, —COOAr, —COOAr',

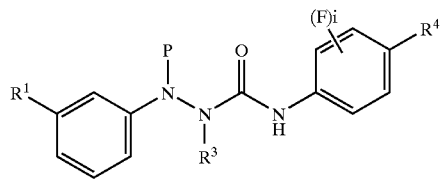

R⁵ is —CHal$_3$, —O(C=O)A or

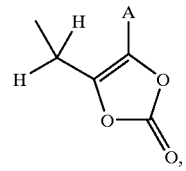

A is H, or an unbranched, branched or cyclic alkyl having 1–20 C atoms,

Ar is phenyl or naphthyl, which is unsubstituted or mono-, di- or trisubstituted by A, OH, OA, NH$_2$, NHA, NA$_2$, NO$_2$, CF$_3$, CN, Hal, NHCOA, COOA, CONH$_2$, CONHA, CONA$_2$, S(O)$_n$A, S(O)$_n$NH$_2$, S(O)$_n$NHA, or S(O)$_n$NA$_2$, Ar' is —(CH$_2$)$_n$—Ar, Het is a mono- or binuclear, saturated, unsaturated or aromatic heterocycle having 1 to 4 N, O and/or S atoms, bonded via N or C, which is optionally unsubstituted or substituted by A, Hal is F, Cl, Br or I, n is 1, 2, 3, 4, 5 or 6, and m is 0 or 1,

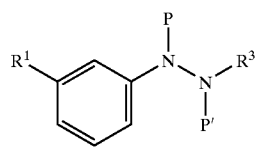

wherein

R³ is unbranched, branched or cyclic alkyl having 1–20 C atoms, in which one or two CH$_2$ groups are optionally each independently of one another replaced by an O or S atom, or is Ar, Ar', X or Hal, X is —(CH$_2$)$_n$—Y, Y is COOA, or

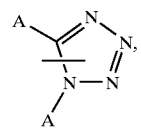

and wherein R¹, P, P', Ar, Ar' and Hal are as defined for formula III, b) converting a compounds of the formula IV to give a compounds of formula V,

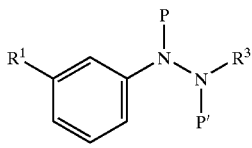

IV

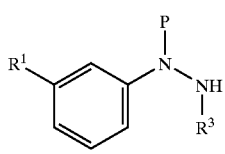

V wherein in both the compounds of formula IV and V, the groups $R_1$, P, P', and $R^3$ are as defined in a)

c) converting a compound of formula V to a compound of formula VI,

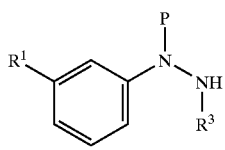

V

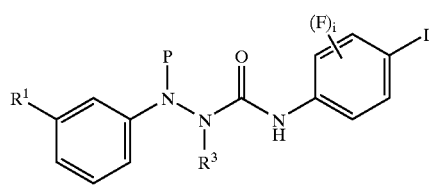

VI wherein in both the compounds of formula V and VI, the groups $R_1$, $R_3$ and P are as defined in a), i is 0, 1, 2, 3 or 4, and I is iodine, or d) converting a compound of formula VI to a compound of the formula VII

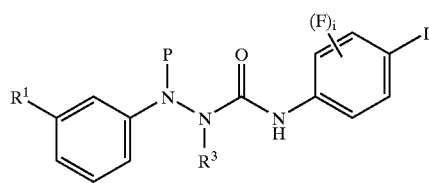

VI

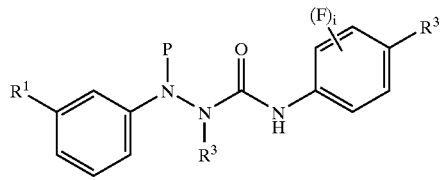

VII wherein in both the compounds of formula VI and VII, the groups $R^1$, $R^3$, P, I, and i are as defined in c), and $R^4$ is phenyl monosubstituted by $S(O)_kA$, $S(O)_kNHA$, $CF_3$, COOA, $CH^2NHA$, CN or OA, wherein k is 0, 1 or 2, and A is as defined in a).

10. A pharmaceutical composition comprising a compound of formula I according to claim 1 and/or a pharmaceutically acceptable salt or solvate thereof and a pharmaceutically acceptable carrier.

11. A method of treating thromboses, myocardial infarct, arteriosclerosis, inflammation, apoplexy, angina pectoris, restenosis after angioplasty, intermittent claudication tumor, and/or tumor metastases comprising administering to a patient in need thereof an effective amount of a pharmaceutical composition according to claim 10.

12. A semicarbazide as claimed in claim 1, which is of the formula

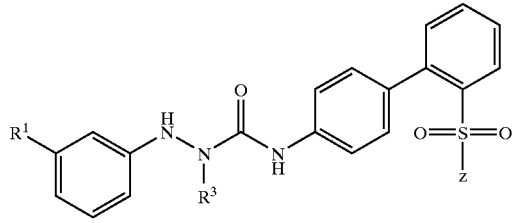

wherein $R^1$ is —C(=NH)—$NH_2$, or —C(=NH)—NH—OH, $R^3$ is an unbranched or branched alkyl having 1–5 C atoms, and z is —$NH_2$, or —$CH_3$.

13. A semicarbazide as claimed in claim 1, which is of the formula

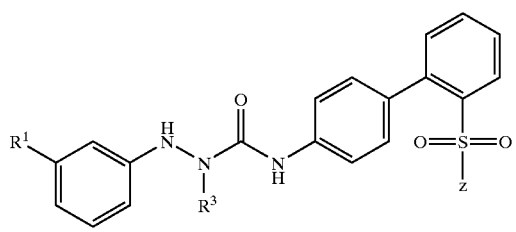

wherein $R_1$ is —C(=NH)—$NH_2$, or —C(=NH)—NH—OH, z is —$NH_2$, or —$CH_3$, and $R_3$ is a branched or cyclic alkyl having 1–7 carbon atoms or Ar or Ar', Ar is phenyl, and Ar' is —$CH_2$—Ar.

14. A semicarbazide, which is of the formula

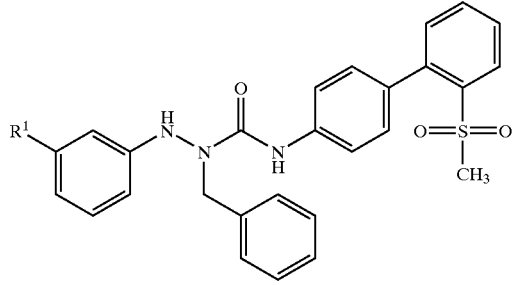

wherein $R^1$ is —C(=NH)=$NH_2$, which is monosubstituted by —COO—$C(A)_2$—$R^5$, —COOA, —COSA, —COOAr, or —COOAr', Ar is phenyl, which is unsubstituted or mono-substituted by A, OA, or F, Ar' is —$CH_2$—Ar, A is H or an unbranched, or branched alkyl or alkenyl having 1–4 C atoms,
R⁵ is —CHal₃, and
Hal is Cl.

15. A semicarbazide, which is of the formula

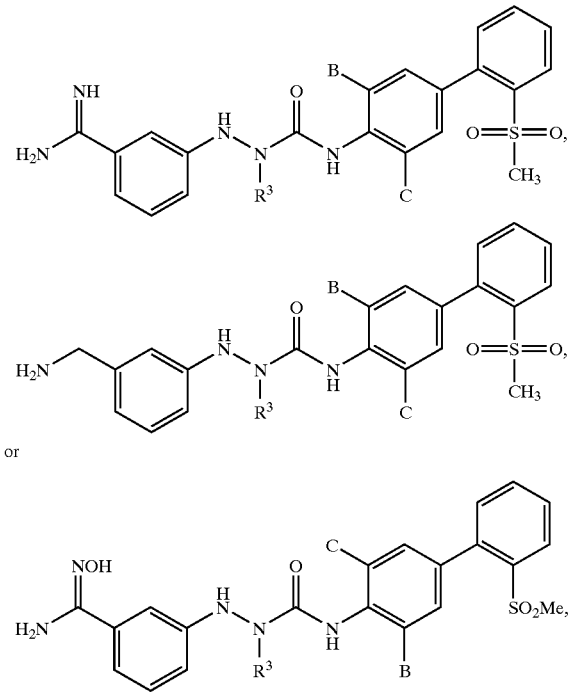

wherein
B and C are each independently H or F, and
R³ is

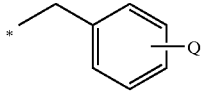

wherein
Q is absent or is $CH_3$, F, Cl, COOH, $CF_3$, or $OCF_3$.

16. A compound which is:
4'-[3-(3-amidinophenyl)-2-(cyclohexylmethyl)carbazoylamino]biphenyl-2-sulfonamide (18),
1-(3-amidinophenyl)-2-(cyclohexylmethyl)-4-(2'-methylsulfonylbiphenyl-4-yl)semicarbazide (19),
2,2,2-trichloroethyl N-[3-[2-benzyl-4-(2'-methylsulfonylbiphenyl-4-yl)semicarbazido]phenyl(iminomethyl)]carbamate (26),
allyl N-[3-[2-benzyl-4-(2'-methylsulfonylbiphenyl-4-yl)semicarbazido]-phenyl(iminomethyl)]carbamate (34),
2-benzyl-1-[3-($N^1$-(methylcarboxy)amidino)phenyl]4-(2'-methylsulfonylbiphenyl-4-yl)semicarbazide (37),
2-benzyl-4-(2'-methylsulfonylbiphenyl-4-yl)-1-[3-($N^1$-(phenylcarboxy)amidino)phenyl]semicarbazide (38),
2-benzyl-1-[3-($N^1$-(isobutylcarboxy)amidino)phenyl]-4-(2'-methylsulfonylbiphenyl-4-yl)semicarbazide (39),
1-methyl-4-piperidinyl N-[3-[2-benzyl-4-(2'-methylsulfonylbiphenyl-4-yl)semicarbazido]phenyl(iminomethyl)]carbamate (42),
2-(4-pyridyl)ethyl N-[3-[2-benzyl-4-(2'-methylsulfonylbiphenyl-4-yl)semicarbazido]phenyl(iminomethyl)]carbamate (43),
5-methyl-2-oxo-1,3-dioxol-4-ylmethyl N-[3-[2-benzyl-4-(2'-methylsulfonylbiphenyl-4-yl)semicarbazido]phenyl(iminomethyl)]carbamate (44),
2-(3-pyridyl)ethyl N-[3-[2-benzyl-4-(2'-methylsulfonylbiphenyl-4-yl)semicarbazido]phenyl(iminomethyl)]carbamate (45),
2-(N,N-diethylamino)ethyl N-[3-[2-benzyl-4-(2'-methylsulfonylbiphenyl-4-yl)semicarbazido]phenyl(iminomethyl)]carbamate (46),
2-(N-morpholinyl)ethyl N-[3-[2-benzyl-4-(2'-methylsulfonylbiphenyl-4-yl)semicarbazido]phenyl(iminomethyl)]carbamate (47),
1-(3-amidinophenyl)-4-(2'-methylsulfonylbiphenyl-4-yl)-2-(3-trifluoromethoxy-benzyl)semicarbazide (56),
4'-[3-(3-amidinophenyl)-2-[2-(1-methyltetrazol-5-yl)ethyl]carbazoylamino]biphenyl-2-sulfonamide (68),
2-Benzyl-1-[3-(N1-ethoxy)-amidino)-phenyl]-4-(2'-methylsulfonylbiphenyl-4-yl)-semicarbazide (90),
2-Benzyl-1-[3-(N1-vinyloxy)-amidino)-phenyl]-4-(2'-methylsulfonylbiphenyl-4-yl)-semicarbazide (91),
2-Benzyl-1-[3-(N1-benzyloxy)-amidino)-phenyl]-4-(2'-methylsulfonylbiphenyl-4-yl)-semicarbazide (92),
2-Benzyl-1-[3-(N1-isopropoxy)-amidino)-phenyl]-4-(2'-methylsulfonylbiphenyl-4-yl)-semicarbazide (93).

17. A compound according to claim 1, which is:
4'-[3-(3-amidinophenyl)-2-propylcarbazoylamino]biphenyl-2-sulfonamide (1),
4'-[3-(3-($N^2$-hydroxyamidino)phenyl)-2-propylcarbazoylamino]biphenyl-2-sulfonamide (2),
4'-[3-(3-amidinophenyl)-2-methylcarbazoylamino]biphenyl-2-sulfonamide (3),
1-(3-amidinophenyl)-2-methyl-4-(2'-methylsulfonylbiphenyl-4-yl)semicarbazide (4),
4'-[3-(3-amidinophenyl)-2-ethylcarbazoylamino]biphenyl-2-sulfonamide (5),
1-(3-amidinophenyl)-2-ethyl4-(2'-methylsulfonylbiphenyl4-yl)semicarbazide (6),
4'-[3-(3-amidinophenyl)-2-isopropylcarbazoylamino]biphenyl-2-sulfonamide (7),
1-(3-amidinophenyl)-2-isopropyl-4-(2'-methylsulfonylbiphenyl-4-yl)semicarbazide (8),
4'-[3-(3-amidinophenyl)-2-butylcarbazoylamino]biphenyl-2-sulfonamide (9),
1-(3-amidinophenyl)-2-butyl-4-(2'-methylsulfonylbiphenyl-4-yl)semicarbazide (10),
4'-[3-(3-amidinophenyl)-2-isobutylcarbazoylamino]biphenyl-2-sulfonamide (11),
1-(3-amidinophenyl)-2-isobutyl4-(2'-methylsulfonylbiphenyl-4-yl)semicarbazide (12),
4'-[3-(3-amidinophenyl)-2-pentylcarbazoylamino]biphenyl-2-sulfonamide (13),
1-(3-amidinophenyl)-4-(2'-methylsulfonylbiphenyl-4-ylamino)-2-pentylsemicarbazide (14),
1-(3-amidinophenyl)-4-(2'-methylsulfonylbiphenyl-4-ylamino)-2-propylsemicarbazide (15),
4'-[3-(3-amidinophenyl)-2-(2-butyl)carbazoylamino]biphenyl-2-sulfonamide (16),
1-(3-amidinophenyl)-2-(2-butyl)-4-(2'-methylsulfonylbiphenyl-4-yl)semicarbazide (17),
4'-[3-(3-amidinophenyl)-2-benzylcarbazoylamino]biphenyl-2-sulfonamide (20),
1-(3-amidinophenyl)-2-benzyl-4-(2'-methylsulfonylbiphenyl-4-yl)semicarbazide (21), 1-(3-N-²-hydroxyamidinophenyl)-2-benzyl-4-(2'-methylsulfonylbiphenyl-4-yl)-semicarbazide (22),
4'-[3-(3-amidinophenyl)-2-phenylcarbazoylamino]biphenyl-2-sulfonamide (23),
1-(3-amidinophenyl)-4-(2'-methylsulfonylbiphenyl-4-yl)-2-phenylsemicarbazide (24),
methyl N-[3-[2-benzyl-4-(2'-methylsulfonylbiphenyl-4-yl)semicarbazido]-phenyl(iminomethyl)]carbamate (25),
S-ethyl N-[3-[2-benzyl-4-(2'-methylsulfonylbiphenyl-4-yl)semicarbazido]-phenyl(iminomethyl)]thiocarbamate (27),
4-methoxybenzyl N-[3-[2-benzyl-4-(2'-methylsulfonylbiphenyl-4-yl)semicarbazido]phenyl(iminomethyl)]carbamate (28),
ethyl N-[3-[2-benzyl-4-(2'-methylsulfonylbiphenyl-4-yl)semicarbazido]-phenyl(iminomethyl)]carbamate (29),
propyl N-[3-[2-benzyl-4-(2'-methylsulfonylbiphenyl-4-yl)semicarbazido]-phenyl(iminomethyl)]carbamate (30),
butyl N-[3-[2-benzyl-4-(2'-methylsulfonylbiphenyl-4-yl)semicarbazido]-phenyl(iminomethyl)]carbamate (31),
isopropyl N-[3-[2-benzyl-4-(2'-methylsulfonylbiphenyl-4-yl)semicarbazido]phenyl(iminomethyl)]carbamate (32),
isobutyl N-[3-[2-benzyl-4-(2'-methylsulfonylbiphenyl-4-yl)semicarbazido]-phenyl(iminomethyl)]carbamate (33),
phenyl N-[3-[2-benzyl-4-(2'-methylsulfonylbiphenyl-4-yl)semicarbazido]-phenyl(iminomethyl)]carbamate (35),
2-fluorophenyl N-[3-[2-benzyl4-(2'-methylsulfonylbiphenyl4-yl)semicarbazido]phenyl(iminomethyl)]carbamate (36),
2-benzyl-1-[3-[N¹-(2-methylcarboxy-2-propoxycarbonyl)amidino]phenyl]-4-(2'-methylsulfonylbiphenyl-4-yl)semicarbazide (40),
2-benzyl-1-[3-[N¹-(1-(methylcarboxy)ethoxycarbonyl)amidino]phenyl]-4-(2'-methylsulfonylbiphenyl-4-yl)semicarbazide (41),
1-(3-amidinophenyl)-2-(2-fluorobenzyl)-4-(2'-methylsulfonylbiphenyl-4-yl)semicarbazide (48),
1-(3-amidinophenyl)-2-(2-methylbenzyl)-4-(2'-methylsulfonylbiphenyl4-yl)semicarbazide (49),
1-(3-amidinophenyl)-2-(2-chlorobenzyl)-4-(2'-methylsulfonylbiphenyl4-yl)semicarbazide (50),
1-(3-amidinophenyl)-2-(3-chlorobenzyl)-4-(2'-methylsulfonylbiphenyl-4-yl)semicarbazide (51),
4-[1-(3-amidinophenylamino)-3-(2'-methylsulfonylbiphenyl-4-yl)ureidomethyl]-benzoic acid (52),
1-(3-amidinophenyl)-2-(3-methylbenzyl)-4-(2'-methylsulfonylbiphenyl-4-yl)semicarbazide (53),
1-(3-amidinophenyl)-4-(2'-methylsulfonylbiphenyl-4-yl)-2-(3-trifluoromethyl-benzyl)semicarbazide (54),
1-(3-amidinophenyl)-4-(2'-methylsulfonylbiphenyl-4-yl)-2-(4-trifluoromethyl-benzyl)semicarbazide (55),
1-(3-amidinophenyl)-2-benzyl-4-(2'-methylsulfonyl-3-fluor-biphenyl-4-yl)-semicarbazide (57),
1-(3-amidinophenyl)-2-(3-trifluormethylbenzyl)-4-(2'-methylsulfonyl-3-fluor-biphenyl-4-yl)-semicarbazide (58),
1-(3-amidinophenyl)-2-(4-trifluoromethylbenzyl)-4-(2'-methylsulfonyl-3-fluor-biphenyl-4-yl)-semicarbazide (59),
1-(3-amidinophenyl)-2-(2-trifluormethylbenzyl)-4-(2'-methylsulfonylbiphenyl-4-yl)-semicarbazide (60),
1-(3-amidinophenyl)-2-(2-trifluormethylbenzyl)-4-(2'-methylsulfonyl-3-fluor-biphenyl-4-yl)-semicarbazide (61),
1-(3-amidinophenyl)-2-benzyl-4-(2'-methylsulfonyl-3,5-difluor-biphenyl-4-yl)-semicarbazide (62),
1-(3-amidinophenyl)-2-(2-trifluormethylbenzyl)-4-(2'-methylsulfonyl-3,5-difluor-biphenyl-4-yl)-semicarbazide (63),
1-(3-amidinophenyl)-2-(3-trifluormethylbenzyl)-4-(2'-methylsulfonyl-3,5-difluor-biphenyl-4-yl)-semicarbazide (64),
1-(3-amidinophenyl)-2-(4-trifluormethylbenzyl)-4-(2'-methylsulfonyl-3,5-difluor-biphenyl-4-yl)-semicarbazide (65),
ethyl 2-[1-(3-amidinophenylamino)-3-(2'-sulfamoylbiphenyl-4-yl)ureido]-acetate (66),
ethyl 3-[1-(3-amidinophenylamino)-3-(2'-sulfamoylbiphenyl-4-yl)ureido]-propionate (67),
4'-[3-(3-amidinophenyl)-2-(2-methoxyethyl)carbazoylamino]biphenyl-2-sulfonamide (69),
4'-[3-(3-amidinophenyl)-2-(methoxymethyl)carbazoylamino]biphenyl-2-sulfonamide (70),
4'-[3-(3-amidinophenyl)-2-(4-methoxybutyl)carbazoylamino]biphenyl-2-sulfonamide (71),
1-(3-aminomethylphenyl)-2-benzyl-4-(2'-methylsulfonylbiphenyl-4-yl)semicarbazide (72),
1-(3-aminomethylphenyl)-4-(2'-methylsulfonylbiphenyl-4-yl)-2-(2-trifluoro-methylbenzyl)semicarbazie (73),
1-(3-aminomethylphenyl)-4-(2'-methylsulfonylbiphenyl-4-yl)-2-(3-trifluoro-methylbenzyl)semicarbazie (74),
1-(3-aminomethylphenyl)-4-(2'-methylsulfonylbiphenyl-4-yl)-2-(4-trifluoro-methylbenzyl)semicarbazie (75),
1-(3-aminomethylphenyl)-2-benzyl-4-(3-fluoro-2'-methylsulfonylbiphenyl-4-yl)semicarbazide (76),
1-(3-aminomethylphenyl)-4-(3-fluoro-2'-methylsulfonylbiphenyl-4-yl)-2-(2-trifluoromethylbenzyl)semicarbazide (77),
1-(3-aminomethylphenyl)-4-(3-fluoro-2'-methylsulfonylbiphenyl-4-yl)-2-(3-trifluoromethylbenzyl)semicarbazide (78),
1-(3-aminomethylphenyl)-4-(3-fluoro-2'-methylsulfonylbiphenyl-4-yl)-2-(4-trifluoromethylbenzyl)semicarbazide (79),
1-(3-aminomethylphenyl)-2-(3-trifluoromethylbenzyl)-4-(2'-methylsulfonylbiphenyl-4-yl)-semicarbazide (80),
1-(3-aminomethylphenyl)-2-(4-trifluoromethylbenzyl)-4-(2'-methylsulfonylbiphenyl-4-yl)-semicarbazide (81),
1-(3-aminomethylphenyl)-2-benzyl-4-(2'-methylsulfonyl-3-fluoro-biphenyl-4-yl)-semicarbazide (82),
1-(3-aminomethylphenyl)-2-(3-trifluoromethylbenzyl)-4-(2'-methylsulfonyl-3-fluoro-biphenyl-4-yl)-semicarbazide (83),
1-(3-aminomethylphenyl)-2-benzyl-4-(2'-methylsulfonylbiphenyl-4-yl)-semicarbazide (84),
1-(3-aminomethylphenyl)-2-(2-trifluoromethylbenzyl)-4-(2'-methylsulfonyl-3-fluoro-biphenyl-4-yl)-semicarbazide (85), 1-(3-aminomethylphenyl)-2-benzyl-4-(2'-methylsulfonyl-3,5-difluoro-biphenyl-4-yl)-semicarbazide (86), 1-(3-aminomethylphenyl)-2-(2-trifluoromethylbenzyl)-4-(2'-methylsulfonyl-3,5-difluoro-biphenyl-4-yl)-semicarbazide (87), 1-(3-aminomethylphenyl)-2-(4-trifluoromethylbenzyl)-4-(2'-methylsulfonyl-3,5-difluoro-biphenyl-4-yl)-semicarbazide (88), 2-Benzyl-1-[3-($N^1$-methoxy)-amidino)-phenyl]-4-(2'-methylsulfonylbiphenyl-4-yl)-semicarbazide (89), 1-[3-(N-Hydroxyamidino)-phenyl]-2-(3-trifluoromethylbenzyl)-4-(2'-methylsulfonylbiphenyl-4-yl)-semicarbazide (94), 1-[3-(N-Hydroxyamidino)-phenyl]-2-(4-trifluoromethylbenzyl)-4-(2'-methylsulfonylbiphenyl-4-yl)-semicarbazide (95), 1-[3-(N-Hydroxyamidino)-phenyl]-2-benzyl-4-(2'-methylsulfonyl-3-fluorobiphenyl-4-yl)-semicarbazide (96), 1-[3-(N-Hydroxyamidino)-phenyl]-2-(3-trifluoromethylbenzyl)-4-(2'-methylsulfonyl-3-fluorobiphenyl-4-yl)-semicarbazide (97), 1-[3-(N-Hydroxyamidino)-phenyl]-2-(4-trifluoromethylbenzyl)-4-(2'-methylsulfonyl-3-fluorobiphenyl-4-yl)-semicarbazide (98), 1-[3-(N-Hydroxyamidino)-phenyl]-2-(2-trifluoromethylbenzyl)-4-(2'-methylsulfonylbiphenyl-4-yl)-semicarbazide (99), 1-[3-(N-Hydroxyamidino)-phenyl]-2-(2-trifluoromethylbenzyl)-4-(2'-methylsulfonyl-3-fluorobiphenyl-4-yl)-semicarbazide (100), 1-[3-(N-Hydroxyamidino)-phenyl]-2-benzyl-4-(2'-methylsulfonyl-3,5-difluorobiphenyl-4-yl)-semicarbazide (101), 1-[3-(N-Hydroxyamidino)-phenyl]-2-(2-trifluoromethylbenzyl)-4-(2'-methylsulfonyl-3,5-difluoro-biphenyl-4-yl)-semicarbazide (102), 1-[3-(N-Hydroxyamidino)-phenyl]-2-(3-trifluoromethylbenzyl)-4-(2-methylsulfonyl-3,5-difluoro-biphenyl-4-yl)-semicarbazide (103), or 1-[3-(N-Hydroxyamidino)-phenyl]-2-(4-trifluoromethylbenzyl)-4-(2-methylsulfonyl-3,5-difluoro-biphenyl-4-yl)-semicarbazide (104).

* * * * *

UNITED STATES PATENT AND TRADEMARK OFFICE
CERTIFICATE OF CORRECTION

PATENT NO. : 6,849,626 B2
DATED : February 1, 2005
INVENTOR(S) : Werner Mederski et al.

It is certified that error appears in the above-identified patent and that said Letters Patent is hereby corrected as shown below:

Column 34,
Line 1, "(phenylcarboxy)[1]midino)" should be -- (phenylcarboxy)amidino --.

Column 35,
Line 61, "methysulfony" should be -- methysulfonyl --.

Column 41,
Line 2, delete the 2nd appearance of "$CH_2NHA$,".
Line 46, "compounds" should be -- compound --.

Column 42,
Lines 1-10, delete
"
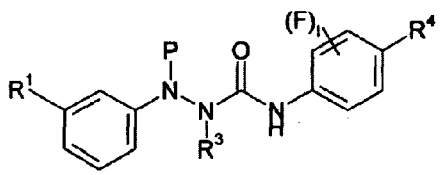
VII
"
and insert
--
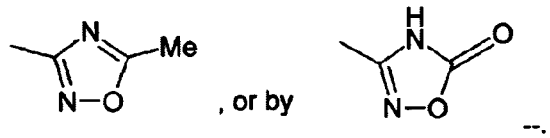
--.

Lines 66 and 67, "compounds" should be -- compound --.

Column 43,
Line 17, "$R_1$" should be -- $R^1$ --.
Line 36, "$R_1, R_3$" should be -- $R^1, R^3$ --.
Line 50, in formula/equation VII: "$R^3$" should be -- $R^4$ --.
Line 60, "$CH^2NHA$" should be -- $CH_2NHA$ --.

UNITED STATES PATENT AND TRADEMARK OFFICE
CERTIFICATE OF CORRECTION

PATENT NO. : 6,849,626 B2
DATED : February 1, 2005
INVENTOR(S) : Werner Mederski et al.

It is certified that error appears in the above-identified patent and that said Letters Patent is hereby corrected as shown below:

Column 48,
Line 34, "semicarbazie" should be -- semicarbazide --.

Signed and Sealed this

Twenty-fifth Day of October, 2005

JON W. DUDAS
*Director of the United States Patent and Trademark Office*